(12) United States Patent
Rubinsky et al.

(10) Patent No.: US 10,143,512 B2
(45) Date of Patent: Dec. 4, 2018

(54) CONTROLLED IRREVERSIBLE ELECTROPORATION

(71) Applicant: The Regents of the University of California, Oakland, CA (US)

(72) Inventors: Boris Rubinsky, El Cerrito, CA (US); Charlotte Daniels, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 551 days.

(21) Appl. No.: 14/679,449

(22) Filed: Apr. 6, 2015

(65) Prior Publication Data

US 2016/0287313 A1 Oct. 6, 2016

Related U.S. Application Data

(63) Continuation of application No. 12/899,389, filed on Oct. 6, 2010.

(60) Provisional application No. 61/262,850, filed on Nov. 19, 2009.

(51) Int. Cl.
| | |
|---|---|
| *A61B 18/14* | (2006.01) |
| *A61N 1/04* | (2006.01) |
| *A61N 1/32* | (2006.01) |
| *A61B 18/00* | (2006.01) |

(52) U.S. Cl.
CPC ............ *A61B 18/14* (2013.01); *A61N 1/0412* (2013.01); *A61N 1/327* (2013.01); *A61B 2018/00613* (2013.01)

(58) Field of Classification Search
CPC .......... A61B 18/14; A61B 2018/00613; A61N 1/0412; A61N 1/327; A61N 1/36002; A61K 9/0009; A61K 41/0047

USPC .......... 604/20, 501; 606/32, 34, 41; 607/72, 607/99, 113, 116; 435/461, 173.6, 285.2
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |

(Continued)

FOREIGN PATENT DOCUMENTS

| | | |
|---|---|---|
| DE | 863111 | 1/1953 |
| DE | 4000893 | 7/1991 |

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Thomas Giuliani
(74) *Attorney, Agent, or Firm* — Karl Bozicevic; Bozicevic, Field & Francis LLP

(57) ABSTRACT

Electrical pulses are applied to tissue in a manner which destroys targeted cells such as cancerous cells while sparing non-targeted cells such as nerve cells. The electrical pulses are controlled within ranges for voltage, wattage and duration of application. Multiple pulses or groups of pulses may be applied to obtain a desired result while maintaining any temperature increase below a level which destroys cells.

14 Claims, 24 Drawing Sheets

(56) References Cited

U.S. PATENT DOCUMENTS

| | | |
|---|---|---|
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |
| 5,403,311 A | 4/1995 | Abele et al. |
| 5,425,752 A | 6/1995 | Vu'Nguyen |
| 5,439,440 A | 8/1995 | Hofmann |
| 5,458,625 A | 10/1995 | Kendall |
| 5,533,999 A | 7/1996 | Hood et al. |
| 5,536,240 A | 7/1996 | Edwards et al. |
| 5,575,811 A | 11/1996 | Reid et al. |
| 5,626,146 A | 5/1997 | Barber et al. |
| 5,634,899 A | 6/1997 | Shapland et al. |
| 5,674,267 A | 10/1997 | Mir et al. |
| 5,702,359 A | 12/1997 | Hofmann |
| 5,718,246 A | 2/1998 | Vona |
| 5,720,921 A | 2/1998 | Meserol |
| 5,778,894 A | 7/1998 | Dorogi et al. |
| 5,782,882 A | 7/1998 | Lerman et al. |
| 5,800,378 A | 9/1998 | Edwards et al. |
| 5,810,762 A | 9/1998 | Hofmann |
| 5,836,905 A | 11/1998 | Lemelson et al. |
| 5,843,026 A | 12/1998 | Edwards et al. |
| 5,873,849 A | 2/1999 | Bernard |
| 5,919,142 A | 7/1999 | Boone et al. |
| 5,947,889 A | 9/1999 | Hehrlein |
| 5,983,131 A | 11/1999 | Weaver et al. |
| 5,991,697 A | 11/1999 | Nelson et al. |
| 5,999,847 A | 12/1999 | Elstrom |
| 6,009,347 A | 12/1999 | Hofmann |
| 6,010,613 A | 1/2000 | Walters et al. |
| 6,016,452 A | 1/2000 | Kasevich |
| 6,041,252 A | 3/2000 | Walker et al. |
| 6,055,453 A | 4/2000 | Hofmann et al. |
| 6,068,650 A | 5/2000 | Nanda et al. |
| 6,085,115 A | 7/2000 | Weaver et al. |
| 6,090,016 A | 7/2000 | Goble et al. |
| 6,102,885 A | 8/2000 | Bass |
| 6,106,521 A | 8/2000 | Blewett et al. |
| 6,109,270 A | 8/2000 | Mah et al. |
| 6,122,599 A | 9/2000 | Mehta |
| 6,132,419 A | 10/2000 | Hofmann |
| 6,159,163 A | 12/2000 | Strauss et al. |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann |
| 6,219,577 B1 | 4/2001 | Brown et al. |
| 6,241,702 B1 | 6/2001 | Lundquist et al. |
| 6,261,831 B1 | 7/2001 | Agee |
| 6,278,895 B1 | 8/2001 | Bernard |
| 6,300,108 B1 | 10/2001 | Rubinsky |
| 6,326,177 B1 | 12/2001 | Schoenbach et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,470,211 B1 | 10/2002 | Ideker et al. |
| 6,482,619 B1 | 11/2002 | Rubinsky et al. |
| 6,493,592 B1 | 12/2002 | Leonard et al. |
| 6,500,173 B2 | 12/2002 | Underwood et al. |
| 6,526,320 B2 | 2/2003 | Mitchell |
| 6,562,604 B2 | 5/2003 | Rubinsky et al. |
| 6,607,529 B1 | 8/2003 | Jones et al. |
| 6,611,706 B2 | 8/2003 | Avrahami et al. |
| 6,613,211 B1 | 9/2003 | McCormick et al. |
| 6,627,421 B1 | 9/2003 | Unger et al. |
| 6,653,091 B1 | 11/2003 | Dunn et al. |
| 6,669,691 B1 | 12/2003 | Taimisto |
| 6,692,493 B2 | 2/2004 | McGovern et al. |
| 6,697,669 B2 | 2/2004 | Dev et al. |
| 6,697,670 B2 | 2/2004 | Chornenky et al. |
| 6,702,808 B1 | 3/2004 | Kreindel |
| 6,795,728 B2 | 9/2004 | Chornenky et al. |
| 6,801,804 B2 | 10/2004 | Miller et al. |
| 6,865,416 B2 | 3/2005 | Dev et al. |
| 6,892,099 B2 | 5/2005 | Jaafar et al. |
| 6,912,417 B1 | 6/2005 | Bernard et al. |
| 6,927,049 B2 | 8/2005 | Rubinsky et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,053,063 B2 | 5/2006 | Rubinsky et al. |
| 7,063,698 B2 | 6/2006 | Whayne et al. |
| 7,130,697 B2 | 10/2006 | Chornenky et al. |
| 7,211,083 B2 | 5/2007 | Chornenky et al. |
| 7,267,676 B2 | 9/2007 | Chornenky et al. |
| 2001/0044596 A1 | 11/2001 | Jaafar |
| 2002/0010491 A1 | 1/2002 | Schoenbach |
| 2002/0055731 A1 | 5/2002 | Atala et al. |
| 2002/0077676 A1 | 6/2002 | Schroeppel et al. |
| 2002/0099323 A1 | 7/2002 | Dev et al. |
| 2002/0138117 A1 | 9/2002 | Son |
| 2002/0193831 A1 | 12/2002 | Smith, III |
| 2003/0009110 A1 | 1/2003 | Tu et al. |
| 2003/0060856 A1 | 3/2003 | Chornenky et al. |
| 2003/0088199 A1 | 5/2003 | Tu et al. |
| 2003/0130711 A1 | 7/2003 | Pearson et al. |
| 2003/0170898 A1 | 9/2003 | Gundersen et al. |
| 2003/0199050 A1 | 10/2003 | Mangano et al. |
| 2003/0208200 A1 | 11/2003 | Palanker et al. |
| 2003/0225360 A1 | 12/2003 | Eppstein et al. |
| 2004/0019371 A1 | 1/2004 | Jaafar et al. |
| 2004/0059389 A1 | 3/2004 | Chornenky et al. |
| 2004/0146877 A1 | 7/2004 | Diss et al. |
| 2004/0153057 A1 | 8/2004 | Davison |
| 2004/0243107 A1 | 12/2004 | Macoviak |
| 2004/0267189 A1 | 12/2004 | Mayor et al. |
| 2005/0043726 A1 | 2/2005 | McHale et al. |
| 2005/0049541 A1 | 3/2005 | Behar et al. |
| 2005/0165393 A1 | 7/2005 | Eppstein |
| 2005/0171523 A1 | 8/2005 | Rubinsky et al. |
| 2005/0171574 A1* | 8/2005 | Rubinsky ............ A61B 18/12 607/2 |
| 2005/0182462 A1 | 8/2005 | Chornenky et al. |
| 2005/0261672 A1 | 11/2005 | Deem et al. |
| 2005/0288730 A1 | 12/2005 | Deem et al. |
| 2006/0015147 A1 | 1/2006 | Persson et al. |
| 2006/0025760 A1 | 2/2006 | Podhajsky |
| 2006/0079883 A1 | 4/2006 | Elmouelhi et al. |
| 2006/0121610 A1 | 6/2006 | Rubinsky et al. |
| 2006/0212078 A1 | 9/2006 | Demarais et al. |
| 2006/0217703 A1 | 9/2006 | Chornenky et al. |
| 2006/0264752 A1 | 11/2006 | Rubinsky et al. |
| 2007/0043345 A1* | 2/2007 | Davalos ............ A61B 18/12 606/32 |
| 2007/0118069 A1 | 5/2007 | Persson et al. |
| 2008/0015571 A1* | 1/2008 | Rubinsky ........ A61B 18/1477 606/42 |
| 2008/0052786 A1 | 2/2008 | Lin et al. |

FOREIGN PATENT DOCUMENTS

| | | |
|---|---|---|
| EP | 0378132 | 7/1990 |
| EP | 0935482 | 5/2005 |
| WO | 96/39531 | 12/1996 |
| WO | 98/14238 | 4/1998 |
| WO | 00/20554 | 4/2000 |
| WO | 01/07583 | 2/2001 |
| WO | 01/07584 | 2/2001 |
| WO | 01/07585 | 2/2001 |
| WO | 01/10319 | 2/2001 |
| WO | 02/78527 | 10/2001 |

(56) References Cited

FOREIGN PATENT DOCUMENTS

| WO | 01/81533 | 11/2001 |
|---|---|---|
| WO | 02/89686 | 11/2002 |
| WO | 02/100459 | 12/2002 |
| WO | 03/99382 | 12/2003 |
| WO | 04/037341 | 5/2004 |

OTHER PUBLICATIONS

Andreason, Electroporation as a Technique for the Transfer of Macromolecules into Mammalian Cell Lines, *J. Tiss. Cult. Meth.*, 15:56-62, 1993.
Baker, et al., Calcium-Dependent Exocytosis in Bovine Adrenal Medullary Cells with Leaky Plasma Membranes, *Nature*, vol. 276, pp. 620-622, 1978.
Barber, Electrical Impedance Tomography Applied Potential Tomography, Advances in Biomedical Engineering, Beneken and Thevenin, eds., IOS Press, 1993.
Beebe, S.J., et al., Nanosecond pulsed electric field (nsPEF) effects on cells and tissues: apoptosis induction and tumor growth inhibition. PPPS—2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Blad, et al., Impedance Spectra of Tumour Tissue in Comparison with Normal Tissue; a Possible Clinical Application for Electrical Impedance Tomography, *Physiol. Meas.* 17 (1996) A105-A115.
Bown, S.G., Phototherapy of tumors. *World J. Surgery*, 1983. 7: p. 700-9.
BPH Management Strategies: Improving Patient Satisfaction, *Urology Times*, May 2001, vol. 29, Supplement 1.
Brown, et al., Blood Flow Imaging Using Electrical Impedance Tomography, *Clin. Phys. Physiol. Meas.*, 1992, vol. 13, Suppl. A, 175-179.
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Coates, C.W., et al., "The Electrical Discharge of the Electric Eel, *Electrophorous Electricus*," Zoologica, 1937, 22(1), pp. 1-32.
Cook, et al., ACT3: A High-Speed, High-Precision Electrical Impedance Tomograph, *IEEE Transactions on Biomedical Engineering*, vol. 41, No. 8, Aug. 1994.
Cowley, Good News for Boomers, *Newsweek*, Dec. 30, 1996/Jan. 6, 1997.
Cox, et al., Surgical Treatment of Atrial Fibrillation: A Review, *Europace* (2004) 5, S20-S-29.
Crowley, Electrical Breakdown of Biomolecular Lipid Membranes as an Electromechanical Instability, *Biophysical Journal*, vol. 13, pp. 711-724, 1973.
Davalos, et al., Tissue Ablation with Irreversible Electroporation, *Annals of Biomedical Engineering*, vol. 33, No. 2, Feb. 2005.
Davalos, et al ., Theoretical Analysis of the Thermal Effects During In Vivo Tissue Electroporation, Bioelectrochemistry, vol. 61, pp. 99-107, 2003.
Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002.
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
Dean, Nonviral Gene Transfer to Skeletal, Smooth, and Cardiac Muscle in Living Animals, *Am J. Physiol Cell Physiol* 289: 233-245, 2005.
Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.
Duraiswami, et al., Boundary Element Techniques for Efficient 2-D and 3-D Electrical Impedance Tomography, *Chemical Engineering Science*, vol. 52, No. 13, pp. 2185-2196, 1997.
Duraiswami, et al., Efficient 2D and 3D Electrical Impedance Tomography Using Dual Reciprocity Boundary Element Techniques, *Engineering Analysis with Boundary Elements* 22, (1998) 13-31.
Duraiswami, et al., Solution of Electrical Impedance Tomography Equations Using Boundary Element Methods, *Boundary Element Technology XII*, 1997, pp. 226-237.
Edd, J., et al., In-Vivo Results of a New Focal Tissue Ablation Technique: Irreversible Electroporaton, *IEEE Trans. Biomed. Eng.* 53 (2006) p. 1409-1415.
Erez, et al., Controlled Destruction and Temperature Distributions in Biological Tissues Subjected to Monoactive Electrocoagulation, *Transactions of the ASME: Journal of Mechanical Design*, vol. 102, Feb. 1980.
Foster, R.S., et al., High-intensity focused ultrasound in the treatment of prostatic disease. *Eur. Urol.*, 1993. 23: 44-7).
Foster, R.S., et al., Production of Prostatic Lesions in Canines Using Transrectally Administered High-Intensity Focused Ultrasound, Eur. Urol., 23:330-336 (1993).
Fox, et al., Sampling Conductivity Images via MCMC, Mathematics Department, Auckland University, New Zealand, May 1997.
Gauger, et al., A Study of Dielectric Membrane Breakdown in the Fucus Egg, *J. Membrane Biol.*, vol. 48, No. 3, pp. 249-264, 1979.
Gehl, et al., In Vivo Electroporation of Skeletal Muscle: Threshold, Efficacy and Relation to Electric Field Distribution, *Biochimica et Biphysica Acta* 1428, 1999, pp. 233-240.
Gençer, et al., Electrical Impedance Tomography: Induced-Current Imaging Achieved with a Multiple Coil System, *IEEE Transactions on Biomedical Engineering*, vol. 43, No. 2, Feb. 1996.
Gilbert, et al., Novel Electrode Designs for Electrochemotherapy, *Biochimica et Biophysica Acta* 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Glidewell, et al., The Use of Magnetic Resonance Imaging Data and the Inclusion of Anisotropic Regions in Electrical Impedance Tomography, *Biomed. Sci. Instrum.* 1993; 29: 251-7.
Gothelf, et al., Electrochemotherapy: Results of Cancer Treatment Using Enhanced Delivery of Bleomycin by Electroporation, *Cancer Treatment Reviews* 2003: 29: 371-387.
Griffiths, et al., A Dual-Frequency Electrical Impedance Tomography System, *Phys. Med. Biol.*, 1989, vol. 34, No. 10, pp. 1465-1476.
Griffiths, The Importance of Phase Measurement in Electrical Impedance Tomography, *Phys. Med. Biol.*, 1987, vol. 32, No. 11, pp. 1435-1444.
Griffiths, Tissue Spectroscopy with Electrical Impedance Tomography: Computer Simulations, *IEEE Transactions on Biomedical Engineering*, vol. 42, No. 9, Sep. 1995.
Gumerov, et al., The Dipole Approximation Method and its Coupling with the Regular Boundary Element Method for Efficient Electrical Impedance Tomography, *Boundary Element Technology XIII*, 1999.
Hapala, Breaking the Barrier: Methods for Reversible Permeabilization of Cellular Membranes, *Critical Reviews in Biotechnology*, 17(2): 105-122, 1997.
Heller, et al., Clinical Applications of Electrochemotherapy, *Advanced Drug Delivery Reviews*, vol. 35, pp. 119-129, 1999.
Ho, et al., Electroporation of Cell Membranes: A Review, *Critical Reviews in Biotechnology*, 16(4): 349-362, 1996.
Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.
Huang, et al., Micro-Electroporation: Improving the Efficiency and Understanding of Electrical Permeabilization of Cells, *Biomedical Microdevices*, vol. 2, pp. 145-150, 1999.

(56) References Cited

OTHER PUBLICATIONS

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Martin et al., "Gene Transfer to Intact Mesenteric Arteries by Electroporation" Journal of Vascular Research, 37:372-380 (2000).

Miklavčic, čet al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris, Ser. III*, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Precision Office TUNA System, When Patient Satisfaction is Your Goal. Product Literature Published by VidaMed, Inc., 11 pages (2001).

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed.* Eng. vol. 2 2000. 157-187.

Schmukler, Robert E. Impedance Spectroscopy of Biological Cells, downloaded from IEEE Xplore website. (Apr. 16, 2009).

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

TUNA—Suggested Local Anesthesia Guidelines. Published by VidaMed, Inc. (1 page) (2001).

Vidamed, Inc., Transurethral Needle Ablation (TUNA): Highlights from Worldwide Clinical Studies, Vidamed's Office TUNA System. (4 pages) (2001).

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

\* cited by examiner

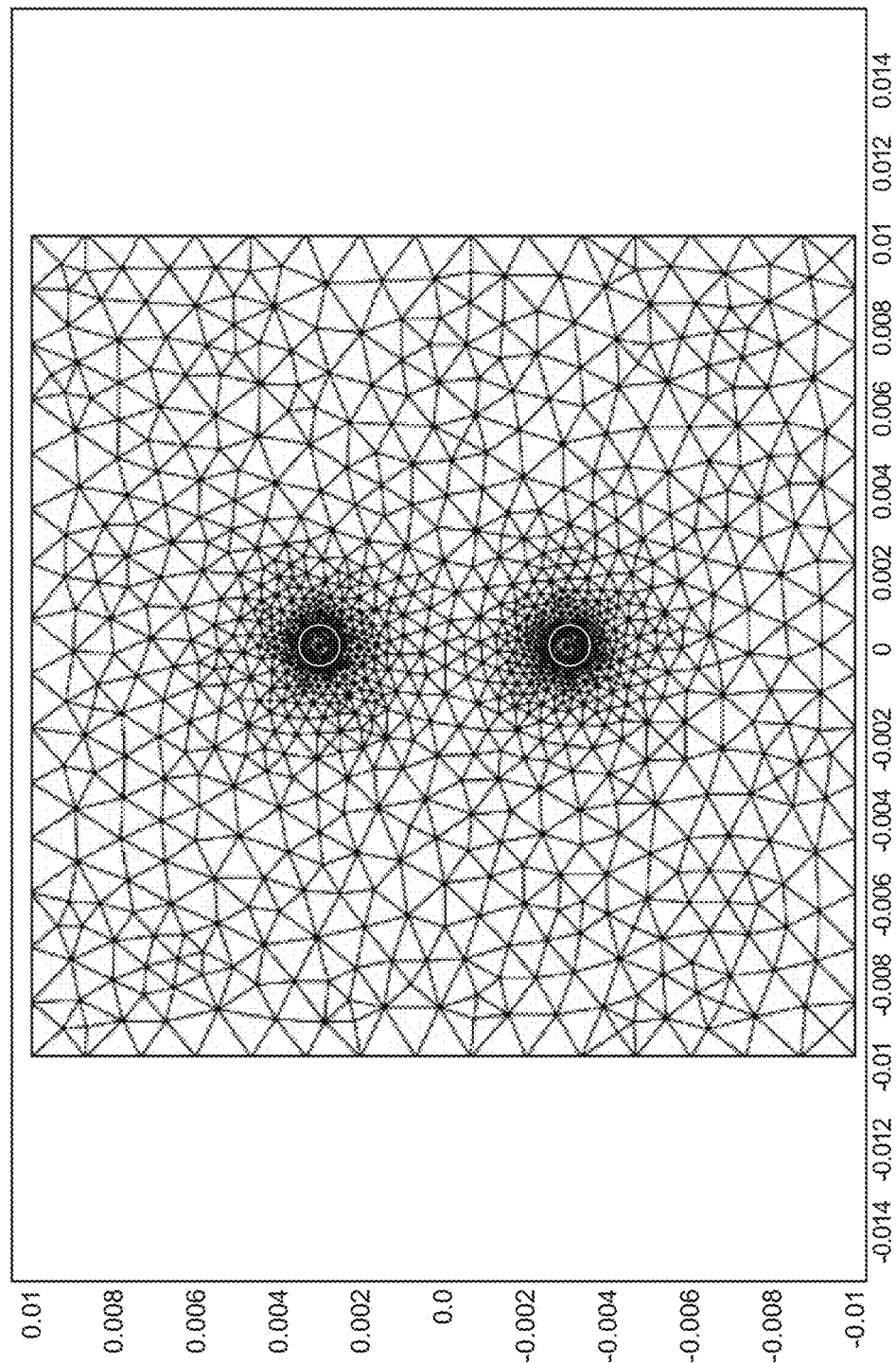

CONTROLLED IRREVERSIBLE ELECTROPORATION

CROSS REFERENCES

This application is a continuation of U.S. patent application Ser. No. 12/899,389 filed Oct. 6, 2010, which application claims the benefit of U.S. Provisional Application No. 61/262,850, filed Nov. 19, 2009, all of which applications are is incorporated herein by reference.

GOVERNMENT RIGHTS

This invention was made with government support under federal grant nos. 403/06 awarded by The National Science Foundation (NSF). The United States Government has certain rights in this invention.

FIELD OF THE INVENTION

The invention relates generally to devices, systems and methods for carrying out electroporation of cells and particularly irreversible electroporation which is carried out in a controlled manner making it possible to selectively destroy certain types of cells.

BACKGROUND OF THE INVENTION

In many medical procedures, such as the treatment of benign or malignant tumors, it is important to be able to ablate the undesirable tissue in a controlled and focused way without affecting the surrounding desirable tissue. Over the years, a large number of minimally invasive methods have been developed to selectively destroy specific areas of undesirable tissues as an alternative to resection surgery. There are a variety of techniques with specific advantages and disadvantages, which are indicated and contraindicated for various applications. For example, cryosurgery is a low temperature minimally invasive technique in which tissue is frozen on contact with a cryogen cooled probe inserted in the undesirable tissue (Rubinsky, B., ed. *Cryosurgery*. Annu. Rev. Biomed. Eng. Vol. 2. 2000. 157-187.). The area affected by low temperature therapies, such as cryosurgery, can be easily controlled through imaging. However, the probes are large and difficult to use. Non-selective chemical ablation is a technique in which chemical agents such as ethanol are injected in the undesirable tissue to cause ablation (Shiina, S., et al., *Percutaneous ethanol injection therapy for hepatocellular carcinoma: results in 146 patients*. AJR, 1993. 160: p. 1023-8). Non-selective chemical therapy is easy to apply. However, the affected area cannot be controlled because of the local blood flow and transport of the chemical species. Elevated temperatures are also used to ablate tissue. Focused ultrasound is a high temperature non-invasive technique in which the tissue is heated to coagulation using high-intensity ultrasound beams focused on the undesirable tissue (Lynn, J. G., et al., *A new method for the generation of use of focused ultrasound in experimental biology*. J. Gen Physiol., 1942. 26: p. 179-93; Foster, R. S., et al., *High-intensity focused ultrasound in the treatment of prostatic disease*. Eur. Urol., 1993. 23: p. 44-7). Electrical currents are also commonly used to heat tissue. Radiofrequency ablation (RF) is a high temperature minimally invasive technique in which an active electrode is introduced in the undesirable tissue and a high frequency alternating current of up to 500 kHz is used to heat the tissue to coagulation (Organ, L. W., *Electrophysiological principles of radiofrequency lesion making*. Appl. Neurophysiol., 1976. 39: p. 69-76). In addition to RF heating traditional Joule heating methods with electrodes inserted in tissue and dc or ac currents are also common, (Erez, A., Shitzer, A. (*Controlled destruction and temperature distribution in biological tissue subjected to monoactive electrocoagulation*) J. Biomech. Eng. 1980:102(1):42-9). Interstitial laser coagulation is a high temperature thermal technique in which tumors are slowly heated to temperatures exceeding the threshold of protein denaturation using low power lasers delivered to the tumors by optical fibers (Bown, S. G., *Phototherapy of tumors*. World. J. Surgery, 1983. 7: p. 700-9). High temperature thermal therapies have the advantage of ease of application. The disadvantage is the extent of the treated area is difficult to control because blood circulation has a strong local effect on the temperature field that develops in the tissue. The armamentarium of surgery is enhanced by the availability of the large number of minimally invasive surgical techniques in existence, each with their own advantages and disadvantages and particular applications. This document discloses another minimally invasive surgical technique for tissue ablation, irreversible electroporation. We will describe the technique, evaluate its feasibility through mathematical modeling and demonstrate the feasibility with in vivo experimental studies.

Electroporation is defined as the phenomenon that makes cell membranes permeable by exposing them to certain electric pulses (Weaver, J. C. and Y. A. Chizmadzhev, *Theory of electroporation: a review*. Bioelectrochem. Bioenerg., 1996. 41: p. 135-60). Electroporation pulses are defined as those electrical pulses that through a specific combination of amplitude, shape, time length and number of repeats produce no other substantial effect on biological cells than the permeabilization of the cell membrane. The range of electrical parameters that produce electroporation is bounded by: a) parameters that have no substantial effect on the cell and the cell membrane, b) parameters that cause substantial thermal effects (Joule heating) and c) parameters that affect the interior of the cell, e.g. the nucleus, without affecting the cell membrane. Joule heating, the thermal effect that electrical currents produce when applied to biological materials is known for centuries. It was noted in the previous paragraph that electrical thermal effects which elevate temperatures to values that damage cells are commonly used to ablate undesirable tissues. The pulse parameters that produce thermal effects are longer and/or have higher amplitudes than the electroporation pulses whose only substantial effect is to permeabilize the cell membrane.

There are a variety of methods to electrically produce thermal effects that ablate tissue. These include RF, electrode heating, and induction heating. Electrical pulses that produce thermal effects are distinctly different from the pulses which produce electroporation. The distinction can be recognizing through their effect on cells and their utility. The effect of the thermal electrical pulses is primarily on the temperature of the biological material and their utility is in raising the temperature to induce tissue ablation through thermal effects.

The effect of the electroporation parameters is primarily on the cell membrane and their utility is in permeabilizing the cell membrane for various applications. Electrical parameters that only affect the interior of the cell, without affecting the cell membrane were also identified recently. They are normally referred to as "nanosecond pulses". It has been shown that high amplitude, and short (substantially shorter than electroporation pulses—nanoseconds versus millisecond) length pulses can affect the interior of the cell and in particular the nucleus without affecting the membrane. Studies on nanosecond pulses show that they are "distinctly different than electroporation pulses" (Beebe S J. Fox P M. Rec L J: Somers K. Stark R H. Schoenbach K H. *Nanosecond pulsed electric field (nsPEF) effects on cells and tissues: apoptosis induction and tumor growth inhibition*. PPPS-2001 Pulsed Power Plasma Science 2001. 28th IEEE International Conference on Plasma Science and 13th IEEE International Pulsed Power Conference. Digest of Technical Papers (Cat. No. 01CH37251). IEEE. Part vol. 1, 2001, pp. 211-15 vol. 1. Piscataway, N.J., USA. Several applications have been identified for nano-second pulses. One of them is for tissue ablation through an effect on the nucleus (Schoenbach, K. H., Beebe, S. J., Buescher, K. S. Method and apparatus for intracellular electro-manipulation U.S. Patent Application Pub No. US 2002/0010491 A1, Jan. 24, 2002). Another is to regulate genes in the cell interior, (Gunderson, M. A. et al. Method for intracellular modification within living cells using pulsed electrical fields—regulate gene transcription and entering intracellular US Patent application 2003/0170898 A1, Sep. 11, 2003). Electrical pulses that produce intracellular effects are distinctly different from the pulses which produce electroporation. The distinction can be recognizing through their effect on cells and their utility. The effect of the intracellular electrical pulses is primarily on the intracellular contents of the cell and their utility is in manipulating the intracellular contents for various uses—including ablation. The effect of the electroporation parameters is primarily on the cell membrane and their utility is in permeabilizing the cell membrane for various applications, which will be discussed in greater detail later.

Electroporation is known for over half a century. It was found that as a function of the electrical parameters, electroporation pulses can have two different effects on the permeability of the cell membrane. The permeabilization of the membrane can be reversible or irreversible as a function of the electrical parameters used. In reversible electroporation the cell membrane reseals a certain time after the pulses cease and the cell survives. In irreversible electroporation the cell membrane does not reseal and the cell lyses. A schematic diagram showing the effect of electrical parameters on the cell membrane permeabilization (electroporation) and the separation between: no effect, reversible electroporation and irreversible electroporation is shown in FIG. 1 (Dev, S. B., Rabussay, D. P., Widera, G., Hofmann, G. A., *Medical applications of electroporation*, IEEE Transactions of Plasma Science, Vol 28 No 1, February 2000, pp 206-223) Dielectric breakdown of the cell membrane due to an induced electric field, irreversible electroporation, was first observed in the early 1970s (Neumann, E. and K. Rosenheck, *Permeability changes induced by electric impulses in vesicular membranes*. J. Membrane Biol., 1972. 10: p. 279-290; Crowley, J. M., *Electrical breakdown of biomolecular lipid membranes as an electromechanical instability*. Biophysical Journal, 1973. 13: p. 711-724; Zimmermann, U., J. Vienken, and G. Pilwat, *Dielectric breakdown of cell membranes*, Biophysical Journal, 1974. 14(11): p. 881-899). The ability of the membrane to reseal, reversible electroporation, was discovered separately during the late 1970s (Kinosita Jr, K. and T. Y. Tsong, *Hemolysis of human erythrocytes by a transient electric field*. Proc. Natl. Acad. Sci. USA, 1977. 74(5): p. 1923-1927; Baker, P. F. and D. E. Knight, *Calcium-dependent exocytosis in bovine adrenal medullary cells with leaky plasma membranes*. Nature, 1978. 276: p. 620-622; Gauger, B. and F. W. Bentrup, *A Study of Dielectric Membrane Breakdown in the Fucus Egg*, J. Membrane Biol., 1979. 48(3): p. 249-264).

The mechanism of electroporation is not yet fully understood. It is thought that the electrical field changes the electrochemical potential around a cell membrane and induces instabilities in the polarized cell membrane lipid bilayer. The unstable membrane then alters its shape forming aqueous pathways that possibly are nano-scale pores through the membrane, hence the term "electroporation" (Chang, D. C., et al., *Guide to Electroporation and Electrofusion*. 1992, San Diego, Calif.: Academic Press, Inc.). Mass transfer can now occur through these channels under electrochemical control. Whatever the mechanism through which the cell membrane becomes permeabilized, electroporation has become an important method for enhanced mass transfer across the cell membrane.

The first important application of the cell membrane permeabilizing properties of electroporation is due to Neumann (Neumann, E., et al., *Gene transfer into mouse lyoma cells by electroporation in high electric fields*. J. EMBO, 1982. 1: p. 841-5). He has shown that by applying reversible electroporation to cells it is possible to sufficiently permeabilize the cell membrane so that genes, which are macromolecules that normally are too large to enter cells, can after electroporation enter the cell. Using reversible electroporation electrical parameters is crucial to the success of the procedure, since the goal of the procedure is to have a viable cell that incorporates the gene.

Following this discovery electroporation became commonly used to reversible permeabilize the cell membrane for various applications in medicine and biotechnology to introduce into cells or to extract from cells chemical species that normally do not pass, or have difficulty passing across the cell membrane, from small molecules such as fluorescent dyes, drugs and radioactive tracers to high molecular weight molecules such as antibodies, enzymes, nucleic acids, HMW dextrans and DNA. It is important to emphasize that in all these applications electroporation needs to be reversible since the outcome of the mass transport requires for the cells to be alive after the electroporation.

Following work on cells outside the body, reversible electroporation began to be used for permeabilization of cells in tissue. Heller, R., R. Gilbert, and M. J. Jaroszeski, *Clinical applications of electrochemotherapy*. Advanced drug delivery reviews, 1999. 35: p. 119-129. Tissue electroporation is now becoming an increasingly popular minimally invasive surgical technique for introducing small drugs and macromolecules into cells in specific areas of the body. This technique is accomplished by injecting drugs or macromolecules into the affected area and placing electrodes into or around the targeted tissue to generate reversible permeabilizing electric field in the tissue, thereby introducing the drugs or macromolecules into the cells of the affected area (Mir, L. M., *Therapeutic perspectives of in vivo cell electropermeabilization*. Bioelectrochemistry, 2001. 53: p. 1-10).

The use of electroporation to ablate undesirable tissue was introduced by Okino and Mohri in 1987 and Mir et al. in 1991. They have recognized that there are drugs for treatment of cancer, such as bleomycin and cys-platinum, which are very effective in ablation of cancer cells but have difficulties penetrating the cell membrane. Furthermore, some of these drugs, such as bleomycin, have the ability to selectively affect cancerous cells which reproduce without affecting normal cells that do not reproduce. Okino and Mori and Mir et al. separately discovered that combining the electric pulses with an impermeant anticancer drug greatly enhanced the effectiveness of the treatment with that drug (Okino, M. and H. Mohri, *Effects of a high-voltage electrical* impulse and an anticancer drug on in vivo growing tumors. Japanese Journal of Cancer Research, 1987. 78(12): p. 1319-21; Mir, L. M., et al., *Electrochemotherapy potentiation of antitumour effect of bleomycin by local electric pulses*. European Journal of Cancer, 1991. 27: p. 68-72). Mir et al. soon followed with clinical trials that have shown promising results and coined the treatment electrochemotherapy (Mir, L. M., et al., *Electrochemotherapy, a novel antitumor treatment: first clinical trial*. C. R. Acad. Sci., 1991. Ser. III 313(613-8)).

Currently, the primary therapeutic in vivo applications of electroporation are antitumor electrochemotherapy (ECT), which combines a cytotoxic nonpermeant drug with permeabilizing electric pulses and electrogenetherapy (EGT) as a form of non-viral gene therapy, and transdermal drug delivery (Mir, L. M., *Therapeutic perspectives of in vivo cell electropermeabilization*. Bioelectrochemistry, 2001. 53: p. 1-10). The studies on electrochemotherapy and electrogenetherapy have been recently summarized in several publications (Jaroszeski, M. J., et al., *In vivo gene delivery by electroporation*. Advanced applications of electrochemistry, 1999. 35: p. 131-137; Heller, R., R. Gilbert, and M. J. Jaroszeski, *Clinical applications of electrochemotherapy*. Advanced drug delivery reviews, 1999. 35: p. 119-129; Mir, L. M., *Therapeutic perspectives of in vivo cell electropermeabilization*. Bioelectrochemistry, 2001. 53: p. 1-10; Davalos, R. V., *Real Time Imaging for Molecular Medicine through electrical Impedance Tomography of Electroporation, in Mechanical Engineering*. 2002, University of California at Berkeley: Berkeley. p. 237). A recent article summarized the results from clinical trials performed in five cancer research centers. Basal cell carcinoma (32), malignant melanoma (142), adenocarcinoma (30) and head and neck squamous cell carcinoma (87) were treated for a total of 291 tumors (Mir, L. M., et al., *Effective treatment of cutaneous and subcutaneous malignant tumours by electrochemotherapy*. British Journal of Cancer, 1998. 77(12): p. 2336-2342).

Electrochemotherapy is a promising minimally invasive surgical technique to locally ablate tissue and treat tumors regardless of their histological type with minimal adverse side effects and a high response rate (Dev, S. B., et al., *Medical Applications of Electroporation*. IEEE Transactions on Plasma Science, 2000. 28(1): p. 206-223; Heller, R., R. Gilbert, and M. J. Jaroszeski, *Clinical applications of electrochemotherapy*. Advanced drug delivery reviews, 1999. 35: p. 119-129). Electrochemotherapy, which is performed through the insertion of electrodes into the undesirable tissue, the injection of cytotoxic drugs in the tissue and the application of reversible electroporation parameters, benefits from the ease of application of both high temperature treatment therapies and non-selective chemical therapies and results in outcomes comparable of both high temperature therapies and non-selective chemical therapies.

In addition, because the cell membrane permeabilization electrical field is not affected by the local blood flow, the control over the extent of the affected tissue by this mode of ablation does not depend on the blood flow as in thermal and non-selective chemical therapies. In designing electroporation protocols for ablation of tissue with drugs that are incorporated in the cell and function in the living cells it was important to employ reversible electroporation; because the drugs can only function in a living cell. Therefore, in designing protocols for electrochemotherapy the emphasis was on avoiding irreversible electroporation. The focus of the entire field of electroporation for ablation of tissue was on using reversible pulses, while avoiding irreversible electroporation pulses, that can cause the incorporation of selective drugs in undesirable tissue to selectively destroy malignant cells. Electrochemotherapy which employs reversible electroporation in combination with drugs, is beneficial due to its selectivity however, a disadvantage is that by its nature, it requires the combination of chemical agents with an electrical field and it depends on the successful incorporation of the chemical agent inside the cell.

An important concern in the studies of electrochemotherapy and electrogenetherapy in living tissue is the effect of electroporation on blood flow. Martin et al., have found that when reversible electroporation is used for introducing genes into cells on the blood vessel wall the blood vessels remain intact and their response to stimuli where indistinguishable from those of control vessels (Martin, J. B., Young, J. L., Benoit, J. N., Dean, D. A., *Gene transfer to intact Mesenteric arteries by electroporation, Journal of vascular research*, 2000, Vol 37:372-380). Ivanusa et al have found using MRI that with certain electroporation pulses, which appear to be in the irreversible electroporation range, that the electroporation transiently but significantly reduced tumor blood flow (Ivanusa, T, Berays, K., Cemazar, M., Jevtic, V, Demsar, F., Sersa, G. *MRI macromolecular contrast agents as indicators of changed tumor blood flow,* Radiol. Oncol. 2001; 35(2): 139-47). These findings are very different from those described here.

Sersa et al performed studies whose goal was to determine the effect of electrochemotherapy, reversible electroporation with bleomycin or cisplatin, on tumor blood flow (Sersa, G., Sentjurc, M., Ivanusa, T, Berays, K., Kotnik, V, Coer, A., Swartz, H. M., Cemazar, M. *Reduced blood flow and axygenation in SA-1 tumours after electrochemotherapy with cisplatin,* Br. J. Cancer, 2002: 87(9):1047-54) (Sersa, G., Cemazar, M., Miklavcic, D. *Tumor blood flow modifying effects of electrochemotherapy: a potential targeted mechanism radiol*. Oncol 2003: 37(1): 43-8). In the first of the papers they report reduced blood flow that persisted for several days when using reversible electroporation with cisplatin. In the second paper they report complete shut down of blood flow after 24 hours when using reversible electroporation with bleomycin and 50% reduction in blood flow when using reversible electroporation with cisplatin.

SUMMARY OF THE INVENTION

A plurality of electrodes which may comprise a first electrode and a second electrode are applied to tissue which tissue is targeted for destruction. The targeted tissue may include cancer cells. The electrodes are used to send electrical current through the tissue in a manner which achieves irreversible electroporation of targeted cells while avoiding irreversible electroporation of non-targeted cells. Parameters which include voltage, wattage, duration of pulses sent through the tissue are controlled and may be monitored to confirm that they are in specific ranges which avoid thermal damage to surrounding cells. Other parameters such as electrode size, shape and position may be adjusted to avoid damage including thermal damage to non-targeted cells while keeping the temperature at 100° C. or less, or 50° C. or less for a period of time that avoids thermal damage. The methodology may use multiple pulses or multiple groups of pulses in order to obtain a desired result which is the irreversible electroporation of targeted cells without the destruction of non-targeted cells such as nerve cells and with no thermal damage to any cells. Specifically, the parameters which include the voltage, wattage, duration and number of electrical pulses are also controlled in a manner so as to maintain the temperature of the tissue below a level which would destroy cells it being understood that time and temperature are related such that higher temperatures can be maintained over shorter time periods without thermal damage.

An aspect of the invention is that a particular type of cell (e.g. identified tumor cells or cancer tumor cells) within an area of tissue may be targeted and destroyed without destroying non-targeted cells within the same tissue and without thermal damage.

These and other objects, advantages, and features of the invention will become apparent to those persons skilled in the art upon reading the details of the device, system and methodology as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 8A and 8B illustrate the mesh used for homogenous (8A) and heterogenous (8B) models.

DETAILED DESCRIPTION OF THE INVENTION

Figure 1A:
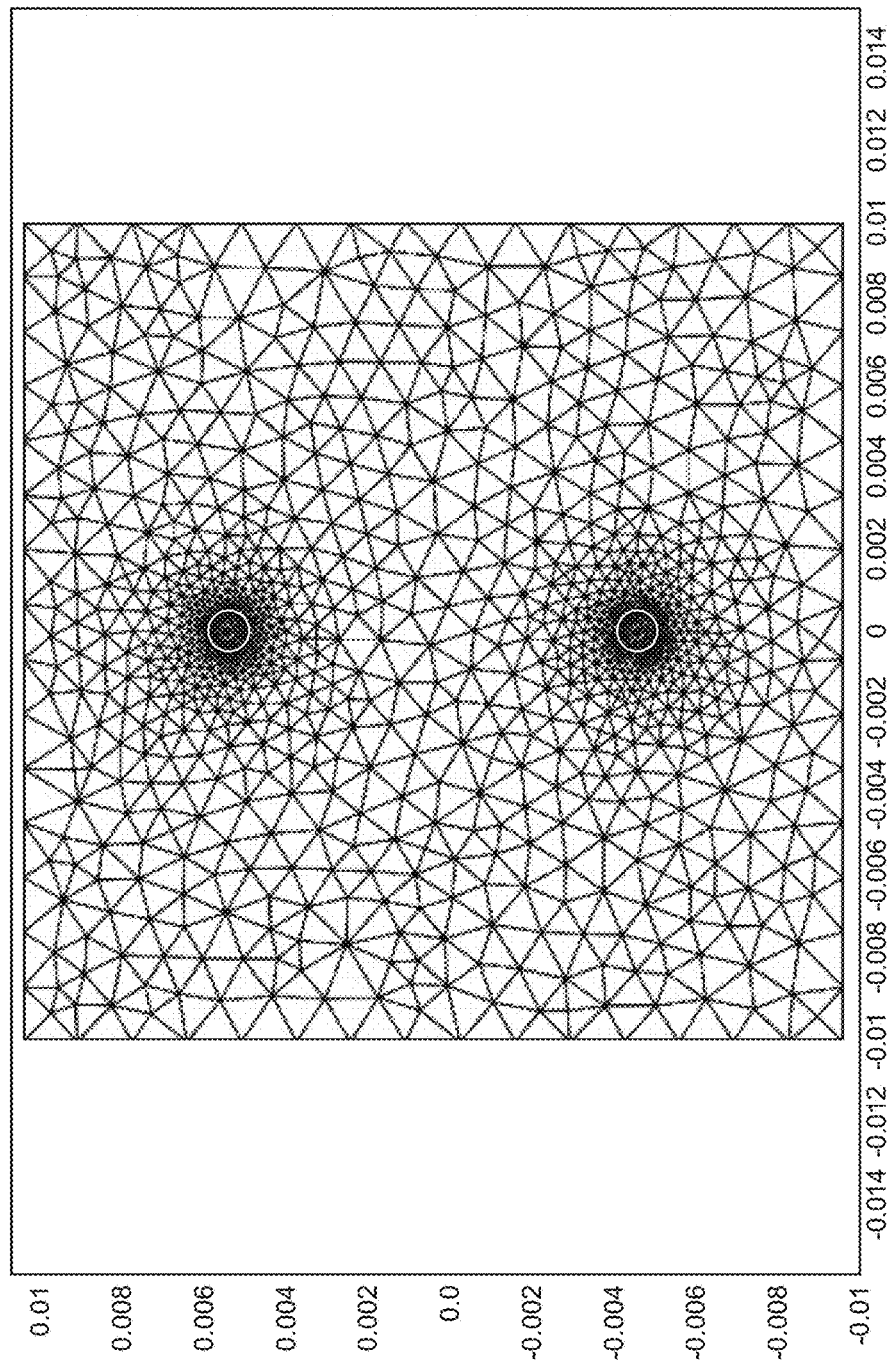
FIGS. 1A and 1B illustrate the mesh used for homogenous (1A) and heterogenous (1B) models.

Before the present devices, systems, and methods of treatment and use are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the pulse" includes reference to one or more pulses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "reversible electroporation" encompasses permeabilization of the cell membrane through the application of electrical pulses across the cell. In "reversible electroporation" the permeabilization of the cell membrane ceases after the application of the pulse and the cell membrane permeability reverts to normal. The cell survives "reversible electroporation." It is used as a means for introducing chemicals, DNA, or other materials into cells.

The term "irreversible electroporation" also encompasses the permeabilization of the cell membrane through the application of electrical pulses across the cell. However, in "irreversible electroporation" the permeabilization of the cell membrane does not cease after the application of the pulse and the cell membrane permeability does not revert to normal. The cell does not survive "irreversible electroporation" and the cell death is caused by the disruption of the cell membrane and not merely by internal perturbation of cellular components. Openings in the cell membrane are created and/or expanded in size resulting in a fatal disruption in the normal controlled flow of material across the cell membrane. The cell membrane is highly specialized in its ability to regulate what leaves and enters the cell. Irreversible electroporation destroys that ability to regulate in a manner such that the cell can not compensate and as such the cell dies.

Specific Embodiments

Models described in the Examples below were created and tested to demonstrate the importance of investigating heterogeneous models with NTIRE and to show that NTIRE treatment methods need to consider the heterogeneous nature of the tissue. Both the model of the prostate and the breast demonstrated the substantial difference between homogeneous and heterogeneous cases. Furthermore, unanticipated information about the effects of electroporation was also discovered. The impact electroporation has on biological structures such as nerves, ducts and blood vessels was previously unknown. This investigation has made clear that nerves can be preserved in treated tissue because of the insulating effect of surrounding myelin layers. Additionally, the Examples show that mammary ducts will also be retained because of myoepithelial cells and their ability to regenerate. Therefore, heterogeneous models are not only important to consider in order to generate an accurate simulation, but also to understand the effects of electroporation on all included biological structures and to improve clinical applications.

A method of targeting cancer cells and subjecting those cells to irreversible electroporation is disclosed. The method involves identifying cancer cells which are to be ablated, killed or in the method of the invention subjected to irreversible electroporation. These cells are identified in a target area wherein the target area comprises an identified nerve tissue. The invention is particularly applicable to killing cancer cells in a target area where the target area comprises nerve tissue which is not cancerous. A first electrode and a second electrode are positioned such that the target area is positioned between the first and second electrodes. Multiple electrodes may be used. Electrical pulses are then applied between the first and second electrodes in sufficient amount to obtain irreversible electroporation of cancer cells in the target area. The voltage, wattage and duration of the electrical pulses are maintained within a distinct range or ranges which avoid damage to nerve tissue in the target area and at the same time avoid thermal damage to cells in the target area and the surrounding area while making it possible to carry out irreversible electroporation of the cancer cells.

The method used can include calculating a voltage, wattage and duration of electrical pulses to be applied in a manner so as to avoid damage to nerve tissue in the target area and avoid thermal damage to cells in the target area. It is also possible to determine the size, shape and relative position of the first electrode and second electrode in a manner so as to avoid damage to nerve tissue in the target area and avoid thermal damage to cells in the target area while subjecting the cancer cells to irreversible electroporation.

In one aspect of the invention there is disclosed a method of treating cancer which comprises identifying nerve tissue in a grouping of biological cells in a target area of a mammal and determining cells in the grouping as being cancer cells. Voltage is applied across the targeted tissue. The method can include continuously detecting a ratio of electric current through the targeted tissue to voltage across the targeted tissue as an indication of degree of electroporation of cells in the targeted tissue. With this information it is possible to adjust a determined magnitude of the applied voltage in accordance with changes in detected magnitude of the current-to-voltage ratio to achieve irreversible electroporation of the cancer cells. With this information it is possible to apply the adjusted voltage to a new target tissue at a point in time significantly after the initial steps have been carried out. Specifically, one may carry out initial testing in order to identify cancer cells within the target area and then continuously detect the ratio of electric current through the targeted tissue to voltage across the targeted tissue as an indication of a degree of electroporation of the cancer cells in the targeted tissue. After this is carried out it is possible to adjust the magnitude of the applied voltage in accordance with the changes detecting in the current-to-voltage ratio to achieve irreversible electroporation of the cancer cells. Once this has been achieved it may not be necessary to repeat these processes each time when applying the adjusted voltage to a new target tissue at a point in time after the other steps have been carried out and the proper parameters such as voltage, wattage, duration and number of electrical pulses has been determined.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Models were generated using numerical analysis executed by a commercially available program Comsol Multiphysics (version 3.4). This initial study utilized 2-dimensional models because these were sufficient to demonstrate the significant difference between homogeneous and heterogeneous models. Two equations were solved simultaneously in Comsol. The first of which was the Laplace equation for potential distribution associated with an electric pulse.

$$-\nabla \cdot d(\sigma \nabla V - J^e) = dQ_j \qquad (1)$$

Where σ is electrical conductivity, V is voltage, $J^e$ is external current density, d is thickness and $Q_j$ is the current source.

For all boundaries the external current density and the current source were set to zero, and thickness was set to one. The electric field was solved in order to illustrate the electrical effects of the electroporation in the particular tissue as listed in Tables 1 and 2. The electric field was solved for in the AC/DC Conductive Media module using a static analysis. Each structure was designated a different electrical conductivity, which corresponded to its representative biological entity. The respective values are shown in Tables I and II.

TABLE I

Values of electrical conductivity for the prostate cancer Conductive Media model

| Structure | Electrical Conductivity ($\sigma$) [S/m] | Reference |
|---|---|---|
| Prostate tissue | 0.42427 | Andreuccetii, et al. |
| Myelin | 3.45E−6 | Villapecellin-Cid, et al. |
| Axon | 1.44 | B. J. Roth et al. |

TABLE II

Values of electrical conductivity for the breast cancer Conductive Media model

| Structure | Electrical Conductivity ($\sigma$) [S/m] | Reference |
|---|---|---|
| Fatty breast tissue | 0.024192 | Andreuccetii, et al. |
| Breast myoepithelial cell | $10^{-7}$ | Hassan N et al. |
| Breast gland | 0.52427 | Andreuccetii, et al. |
| Breast tumor | 2.309 | A. M. Campbell et al. |
| Blood | 0.30709 | Andreuccetii, et al. |

The thermal effects of electroporation were determined from the solution of the Pennes bioheat equation, which was solved simultaneously as the electrical potential equation. The Pennes bioheat equation took the following form:

$$\nabla \cdot (k\nabla T) + \rho_b w_b c_b (T_a - T) + q''' = \rho c_p \frac{\partial T}{\partial t} \quad (2)$$

Where k is the thermal conductivity, T is the temperature, wb is the blood perfusion, cb is the heat capacity of blood, Ta is the arterial temperature, $\rho$ is the tissue density, cp is the tissue heat capacity and $q''' = Q_{met} + Q_{ext}$. Where Qmet is the metabolic heat generation, which is assumed to be negligible here. Also, $Q_{max} = \sigma |\nabla \phi|^2$, which accounts for Joule heating, where $\emptyset$ is electrical potential and $\sigma$ is electrical conductivity of the tissue.

Heat transfer in living organisms is more complex than other circumstances. Metabolism and blood flow are important in addition to conduction, convection, radiation and evaporation. For this reason, the bioheat equation, which includes terms that account for blood flow and metabolism, was used. In addition, the bioheat equation solves for the temperature and ascertains the impact of the Joule effect. The result of the bioheat equation determines if the tumor was being treated also by resistive heating, or only irreversible electroporation.

The values utilized in the bioheat equation for the corresponding structures in the prostate and the breast are shown in Tables III, IV and V.

TABLE III

Values for the prostate cancer Bioheat model

| Structure | Thermal Conductivity (k) [W/mK] | Specific Heat (c) [J/kgK] | Density ($\rho$) [kg/m$^3$] | Reference |
|---|---|---|---|---|
| Prostate tissue | 0.561 | 3600 | 1045 | Yusheng Feng et al. [21] |
| Nerve (axon and myelin) | 0.503 | 3600 | 1043 | S. DeMarco et al. |

TABLE IV

Values for the breast cancer Bioheat model

| Structure | Thermal Conductivity (k) [W/mK] | Specific Heat (c) [J/kgK] | Density ($\rho$) [kg/m$^3$] | Reference |
|---|---|---|---|---|
| Fatty breast tissue | 0.25 | 2522.5 | 900 | Howorka K. et al.; M. P. Robinson et al.; F. Fidanza |
| Breast gland | 0.41 | 3492 | 1030 | F. O. Dosekun; M. A. Kolka et al.; C. R. Moreira et al. |
| Breast tumor | 0.48 | 2926 | 1186 | Kwok et al.; P. Prakash et al.; B. J. Roth et al. |

TABLE V

Values for human blood flow in the prostate and breast cancer Bioheat models

| Structure | Perfusion Rate [1/s] | Thermal Conductivity (k) [W/mK] | Specific Heat (c) [J/kgK] | Density ($\rho$) [kg/m$^3$] | Reference |
|---|---|---|---|---|---|
| Blood | 0.002 | 0.391 | 3640 | 1000 | L. Sun et al.; J. Valvano et al.; S. Belov; Elad Maor et al. |

Models

Five models were utilized to demonstrate the differences between heterogeneous and homogeneous tissues treated with electroporation with an application that is typical to the current implementation of the method in animal models (B. Al-Sakere et al., "Tumor Ablation with Irreversible Electroporation," PLoS ONE, vol. 2, 2007, p. e1135; R. V. Davalos, B. Rubinsky, and L. M. Mir, "Theoretical analysis of the thermal effects during in vivo tissue electroporation," Bioelectrochemistry, vol. 61, October 2003, pp. 99-107). The electrodes were taken to have a diameter of one mm. The electrodes were placed at a distance of one cm, center to center. For boundary conditions, in each case a uniform voltage was imposed on each electrode and a voltage difference of 2000 V was imposed between each electrode.

Case 1a: (2 cm×2 cm) Prostate tissue with two electrodes separated by 1 cm

Case 1b: A nerve (axon with myelin sheath) in the center of (2 cm×2 cm) prostate tissue with two electrodes separated by 1 cm. The nerve is modeled as a structure of a circular axon surrounded by a uniform layer of myelin. The axon radius was 0.1 mm (A. Takenaka et al., "Variation in course of cavernous nerve with special reference to details of topographic relationships near prostatic apex: Histologic study using male cadavers," *Urology*, vol. 65, January 2005, pp. 136-142) and the thickness of the myelin surrounding it was 0.02 mm (J. Schroder, "Altered ratio between axon diameter and myelin sheath thickness in regenerated nerve fibers," Brain Research, vol. 45, October 1972, pp. 49-65). The axon and myelin structure was centered within the square section of prostate tissue.

Case 1c: A blood vessel in the center of (2 cm×2 cm) prostate tissue with two electrodes separated by 1 cm. The blood vessel was 5E-5m in radius and was placed in the center of a square section of prostate tissue.

Case 2: (2 cm×2 cm) fatty breast tissue with two electrodes separated by 1 cm

Case 2b: A duct in the center of (2 cm×2 cm) fatty breast tissue with two electrodes separated by 1 cm. We used in the model a gland surrounded by myoepithelial. The breast gland was 0.7 mm in radius (J. Rusby et al., "Breast duct anatomy in the human nipple: three-dimensional patterns and clinical implications," Breast Cancer Research and Treatment, vol. 106, January 2007, pp. 171-9) and the surrounding layer of myoepithelial cells were 0.13 mm in thickness. The gland and myoepithelial cells were centered within a square section of breast tissue.

The model includes a rectangular cross section of tissue (4 cm2 for the prostate and the breast), large enough to account for fringe effects of the electric field. Electrodes conductive only at the tips are utilized in vivo, so they were represented as points in the models. All models were evaluated at a voltage potential difference between the electrodes of 2000V. Each model simulated a single voltage pulse of length 0.1 ms, and the temperature evaluated at time steps of 0.1E-4s.

There were two sets of boundary conditions generated; one set for the Laplace equation and another for the Pennes bioheat equation. For the Laplace equation, the edges of the tissue sample were treated as electrically insulating.

$$\frac{\partial \phi}{\partial n} = 0 \quad (3)$$

Where ø is potential. The remaining structures were prescribed continuity boundary conditions.

$$n \cdot (J_1 - J_2) = 0 \quad (4)$$

Where n is the normal vector and J is the current density. For the bioheat equation, the edges of the tissue were set to body temperature.

$$T = 310.15K \quad (5)$$

The remaining structures were prescribed continuity boundary conditions.

Results and Discussion

Figure 1B:
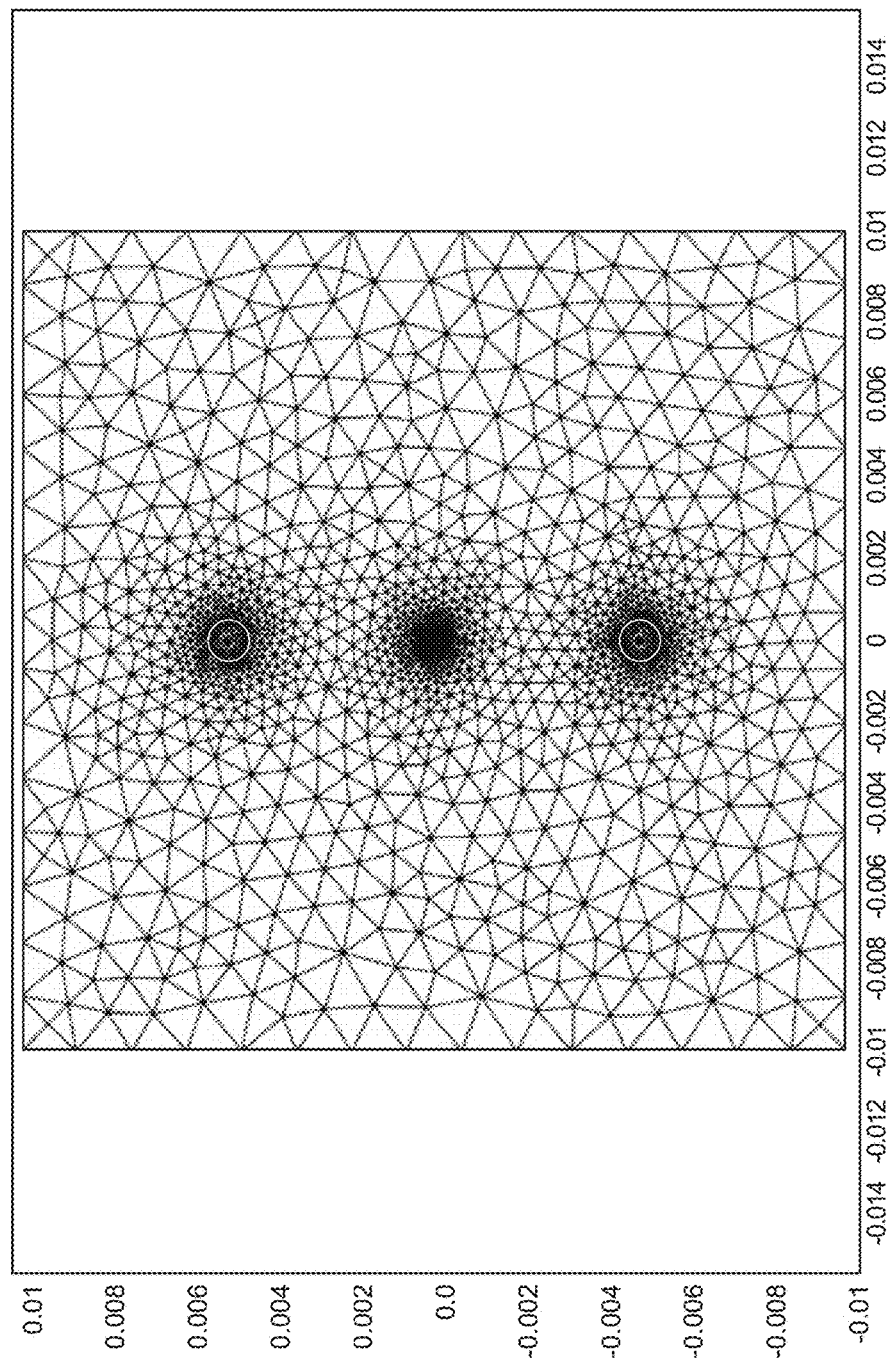

FIGS. 1A and 1B illustrate the mesh that was used for the homogeneous and the heterogeneous models. It is important to note that the mesh becomes more defined around the boundaries of the electrodes. This ensures accurate results in the vicinity of the electrodes and captures even the smallest temperature difference on the micron scale. This is also true of the mesh used for the heterogeneous model. The mesh is extra fine around the boundaries of the inhomogeneity as well as the electrodes.

Figure 2A:
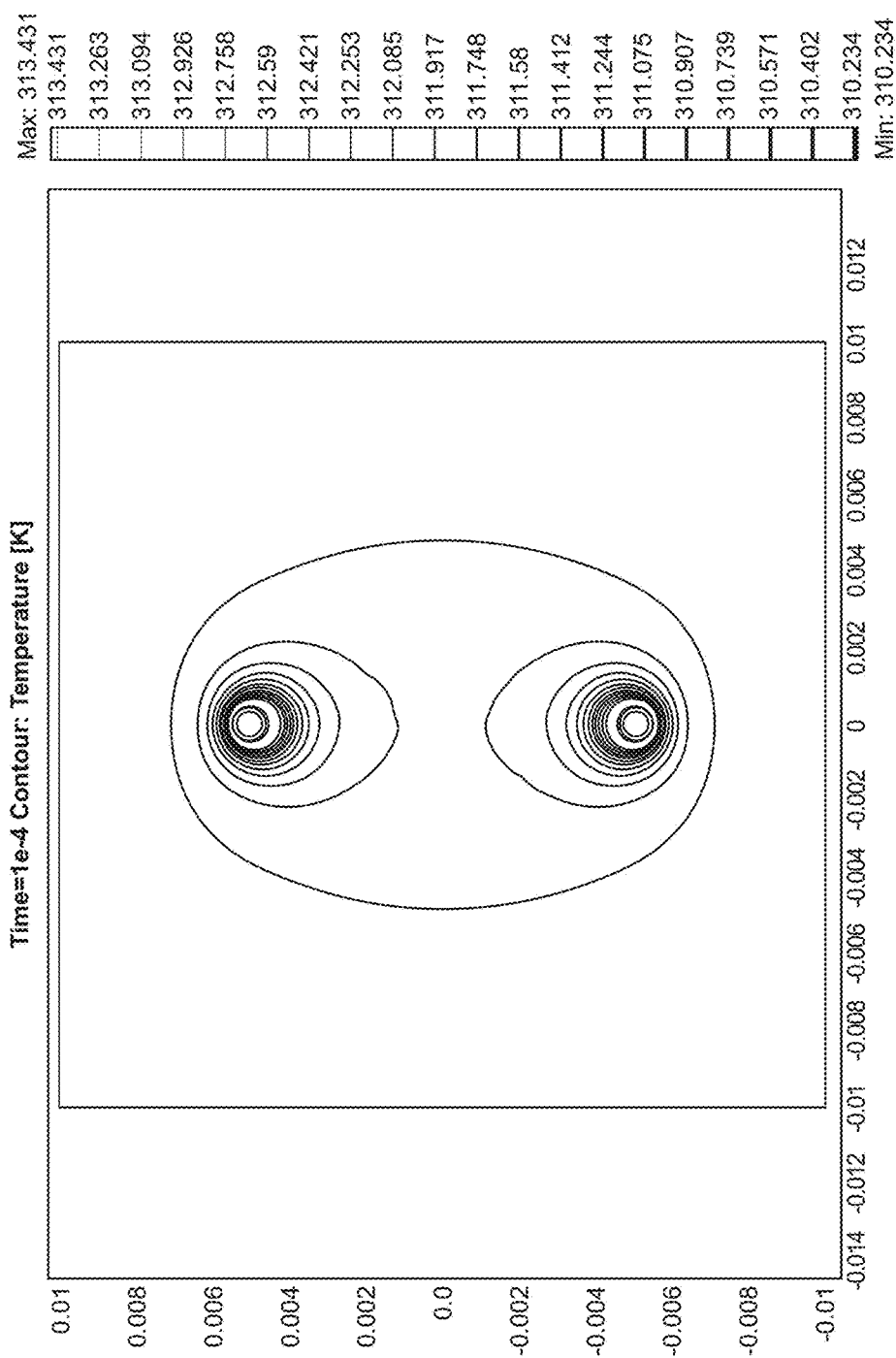
FIGS. 2A and 2B show the temperature distribution in the homogeneous (2A) and heterogenous (2B) models for prostate tissue with two electrodes.
Figure 2B:
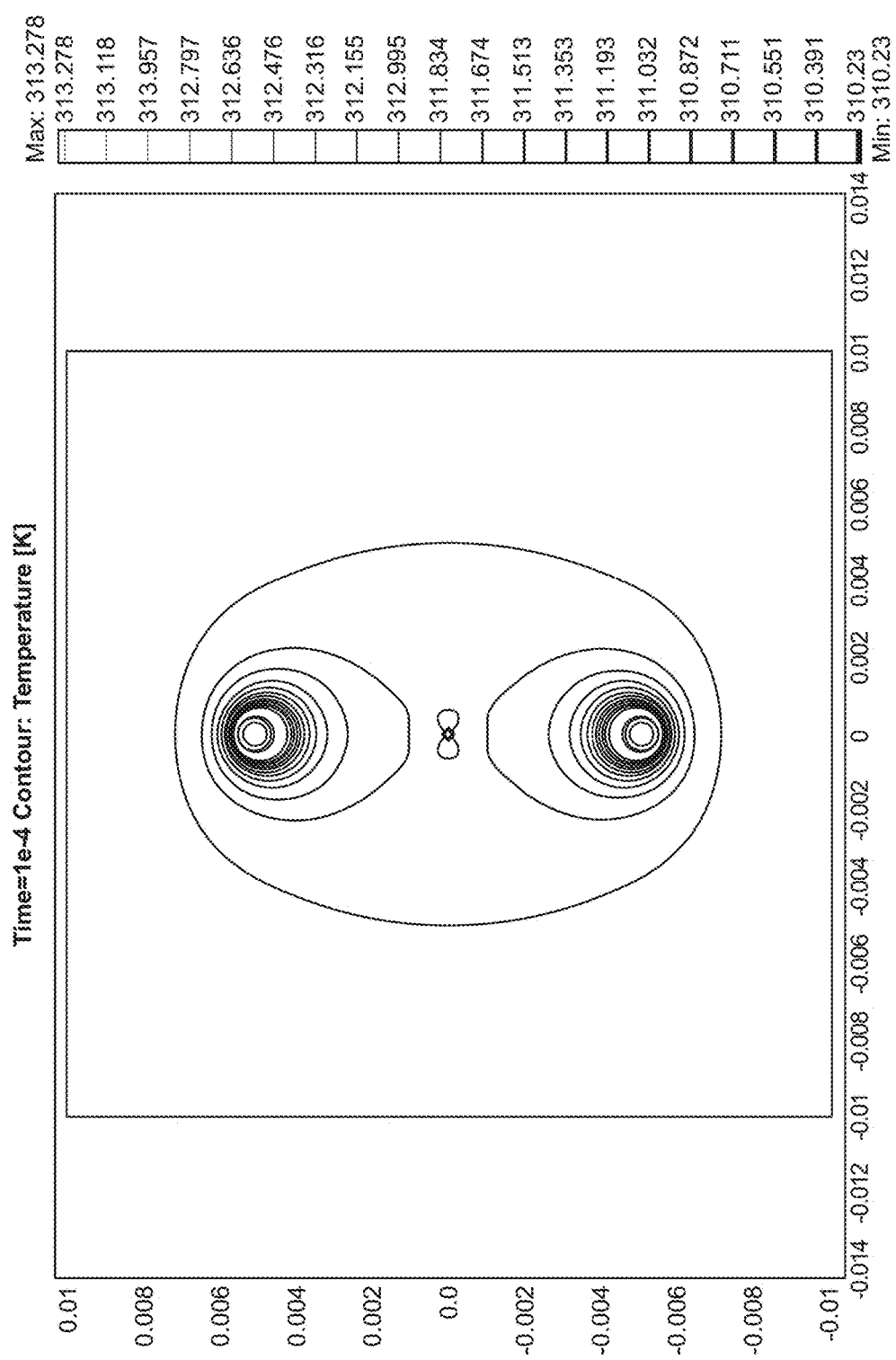
Figure 3A:
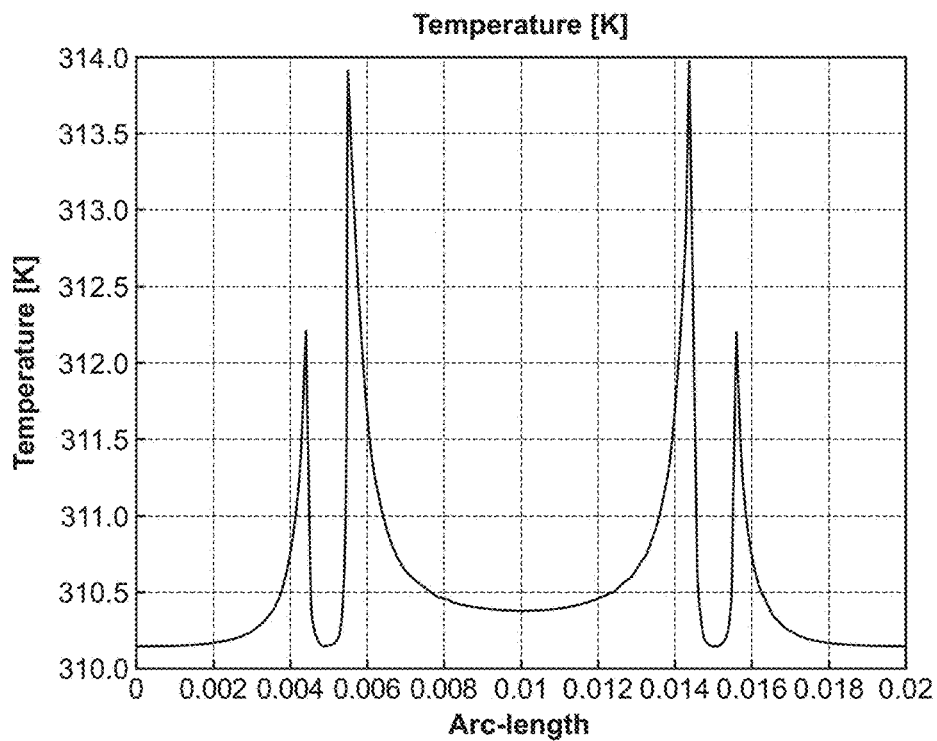
FIG. 3 includes four graphs which show temperature changes where graphs 3A and 3C show the changes with respect to homogeneous tissue and graphs 3B and 3D show temperature changes with heterogeneous tissue.
Figure 3B:
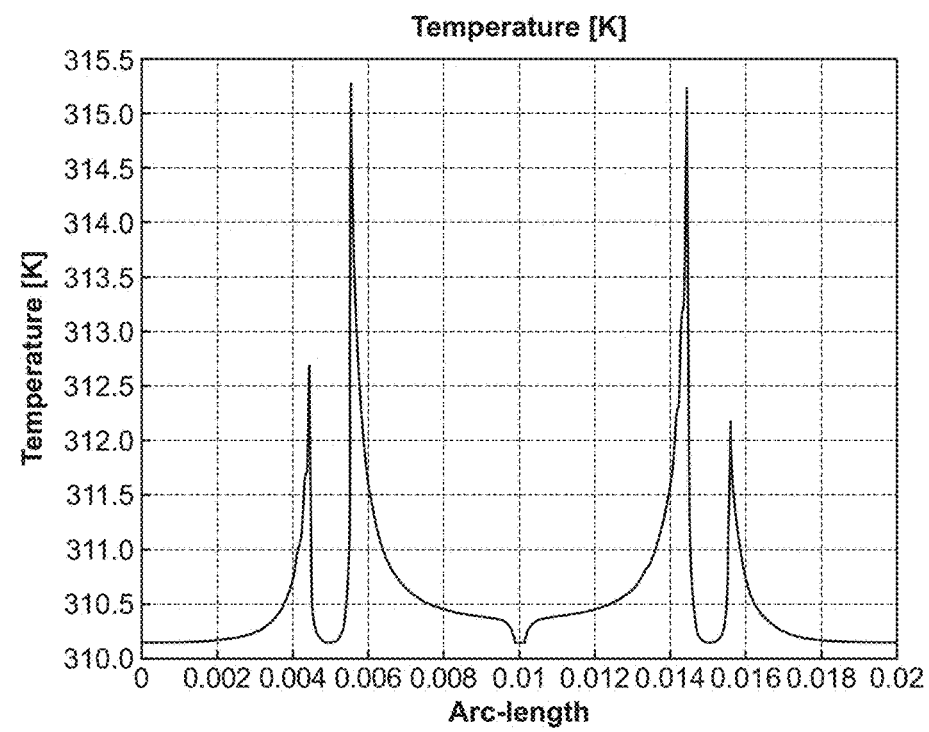

FIGS. 2A and 2B show the temperature distribution in the homogeneous and heterogeneous models of prostate tissue with two electrodes of voltage potential difference 2000V at the end of the application of a single pulse. The figures plot isothermal lines and the details of the temperature distribution can be found in FIGS. 3A, 3B, 3C and 3D. The elevated temperature reaches a maximum of 313.431K in the homogeneous case. However, this is only within nanometers of the electrode. Nevertheless, even the tissue near the electrode doesn't experience thermal damage. In fact, no tissue in the homogeneous case experiences thermal damage. This is because a temperature of 360.15K represents the upper limit before thermal damage occurs. The highest temperature occurs on either sides of the electrode, as can be seen by FIG. 3A.

Figure 3C:
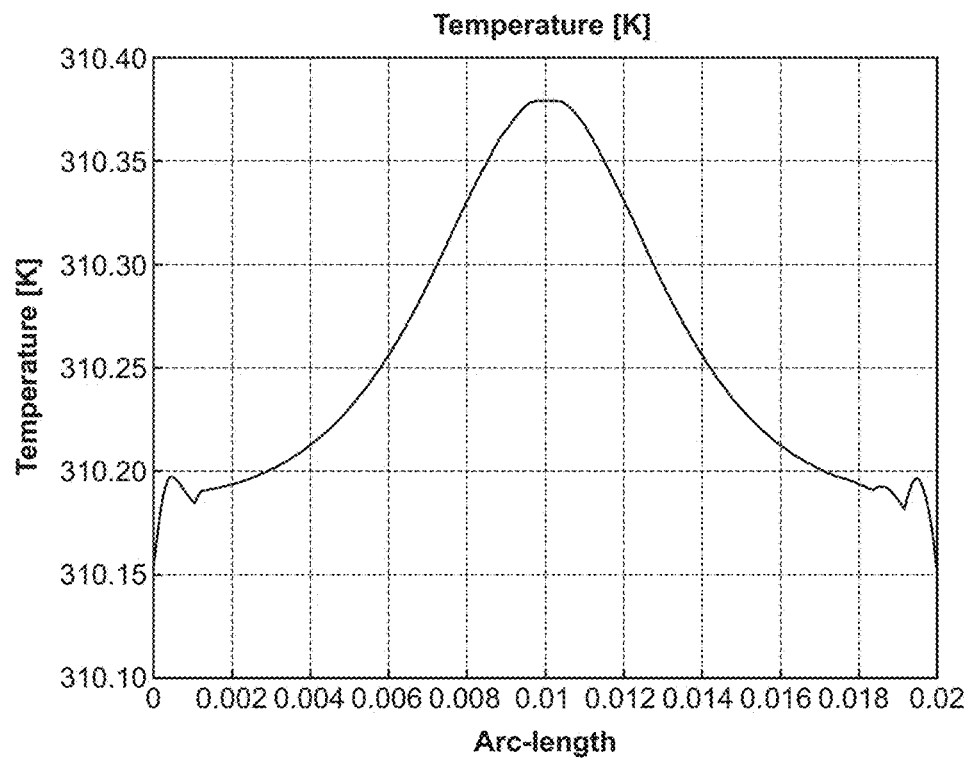
Figure 3D:
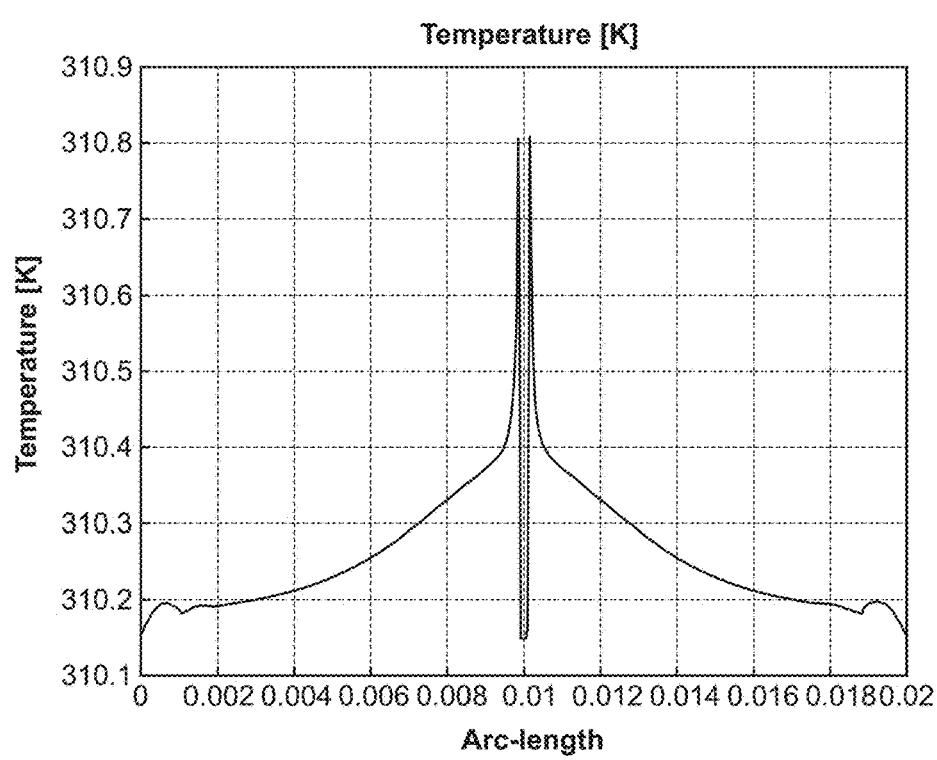

The heterogeneous plot in FIG. 2B includes a nerve (axon and myelin) within the prostate tissue. The axon radius was 0.1 mm (A. Takenaka et al., "Variation in course of cavernous nerve with special reference to details of topographic relationships near prostatic apex: Histologic study using male cadavers," *Urology*, vol. 65, January 2005, pp. 136-142) and the thickness of the myelin surrounding it was 0.02 mm (J. Schroder, "Altered ratio between axon diameter and myelin sheath thickness in regenerated nerve fibers," *Brain Research*, vol. 45, October 1972, pp. 49-65). The axon and myelin structure was centered within the square section of prostate tissue. The difference between the heterogeneous and homogeneous cases can be seen in the temperature range. The homogeneous model ranges from nearly body temperature, 310.234K, to 313.431K. However, the heterogeneous model has a slightly lower temperature throughout, ranging from 310.23K to 313.278K. From the maximum temperature reached in both the heterogeneous cases, it is apparent that it does not experience thermal damage either. Therefore, the prostate tissue in these models only experiences electroporation. It is interesting to note that the main difference between the homogeneous and heterogeneous cases is the dip in the temperature at the center of the plot in the heterogeneous case, where the nerve is located. This dip does not exist in the homogeneous graphs (FIGS. 3A and 3C). The difference in the temperature distribution between these two plots shows the importance of taking heterogeneous models into account for an accurate portrayal.

Figure 4A:
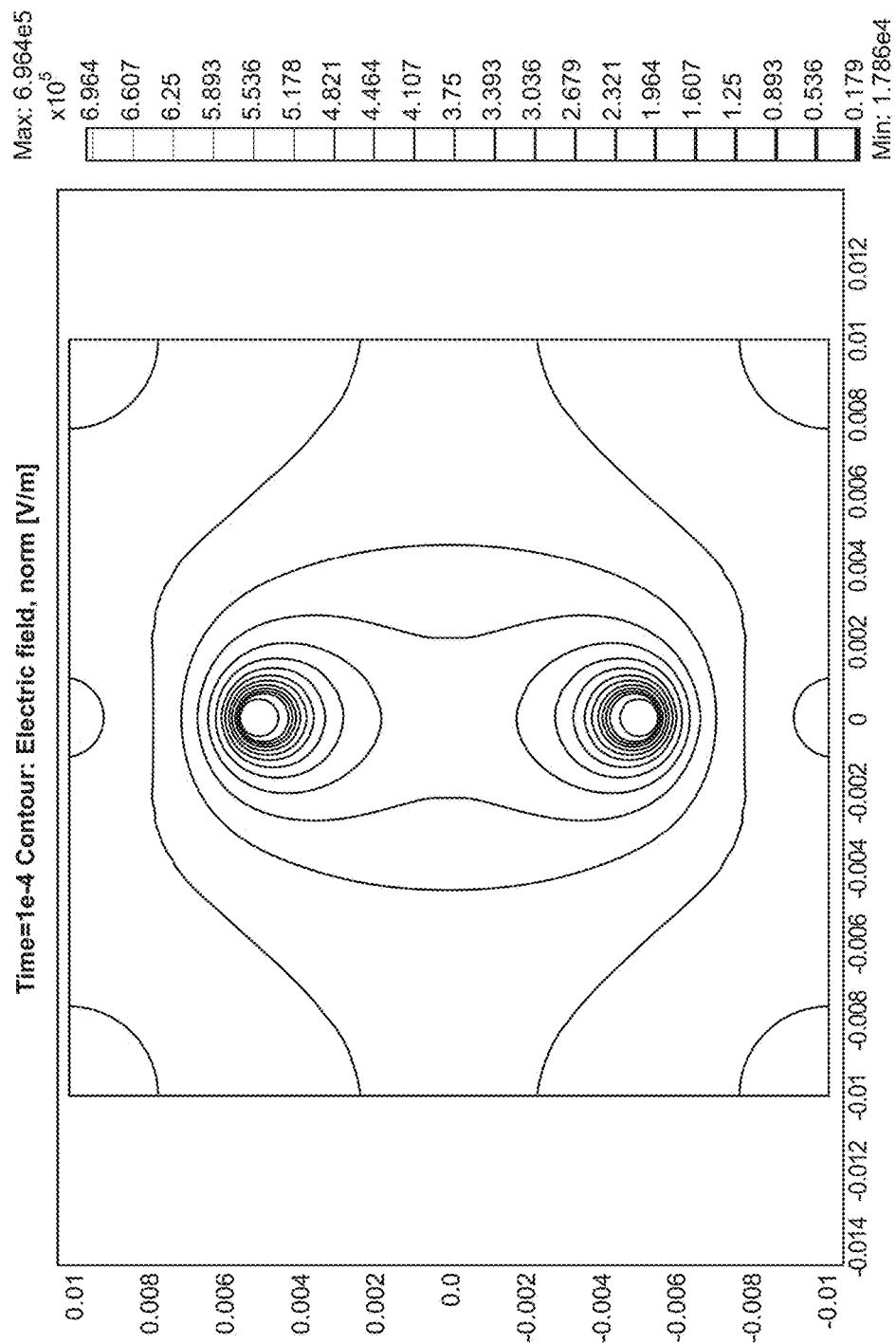
FIGS. 4A and 4B show the temperature distribution in the homogeneous (4A) and heterogenous (4B) models for prostate tissue with two electrodes.
Figure 4B:
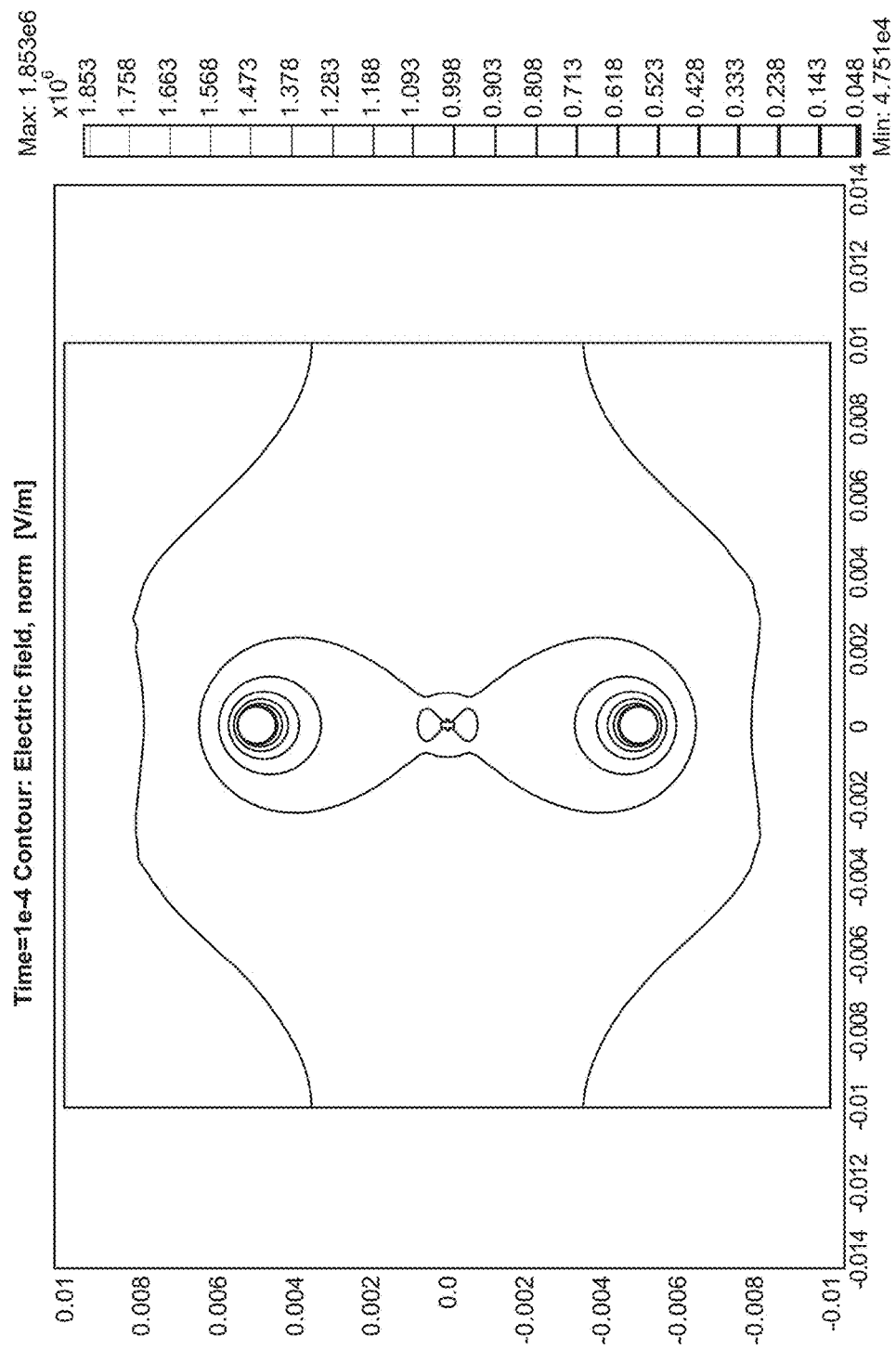

The plot in FIGS. 4A and 4B displays lines of constant electrical field in prostate tissue.

The detailed field distribution can be found in FIGS. 5A, 5B, 5C and 5D.

The maximum electric field occurs at the electrodes and takes a value of $$6.964E5 \frac{V}{m}.$$

Figure 5A:
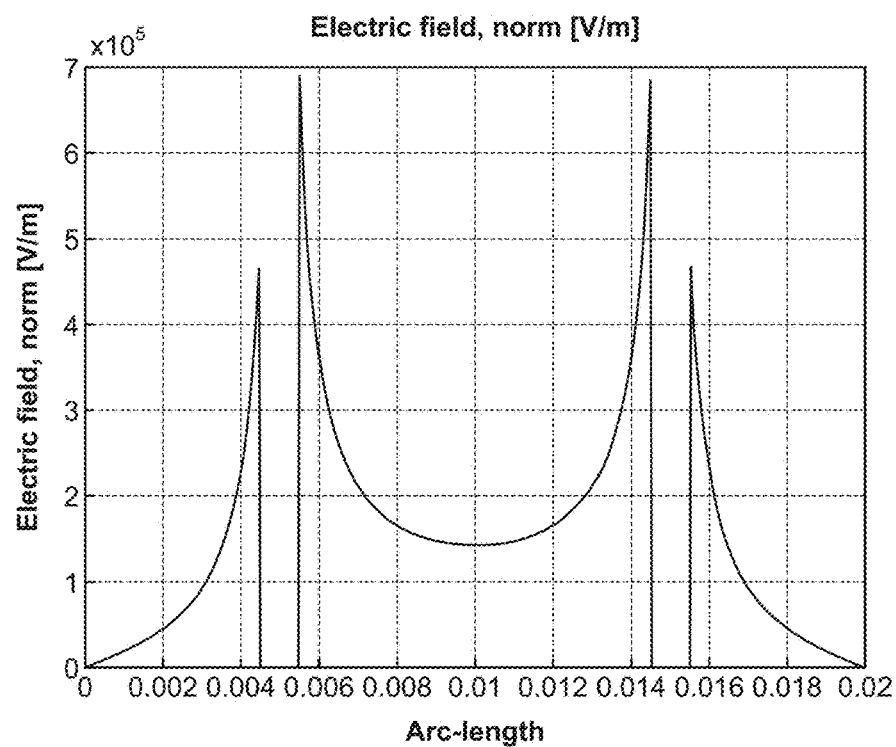
FIG. 5 includes four graphs which show temperature changes where graphs 5A and 5C show the changes with respect to homogeneous tissue and graphs 5B and 5D show temperature changes with heterogeneous tissue.
Figure 5B:
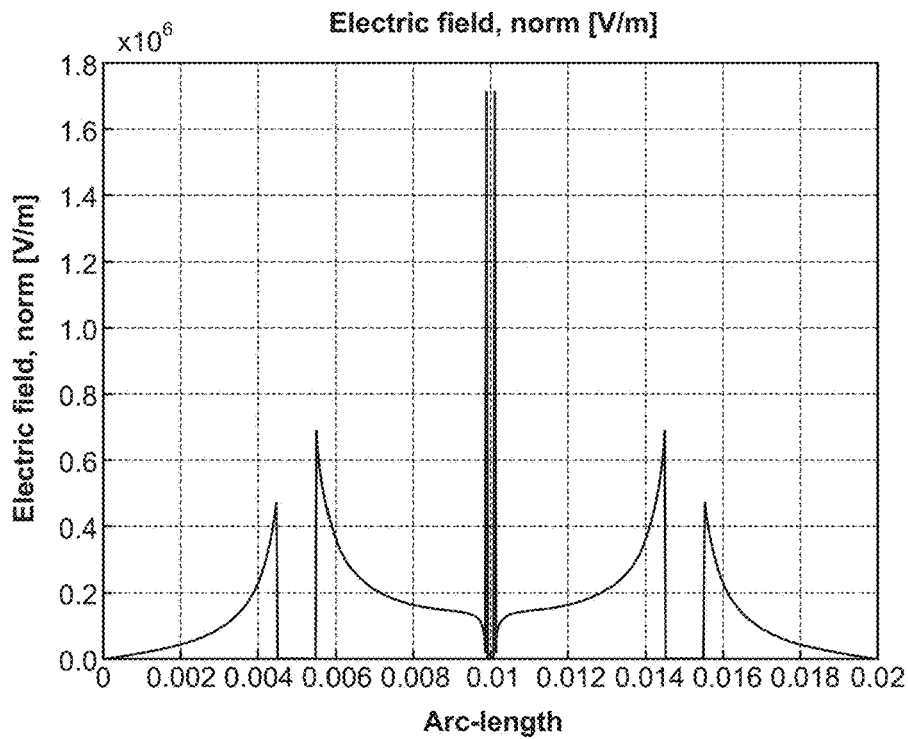
Figure 5C:
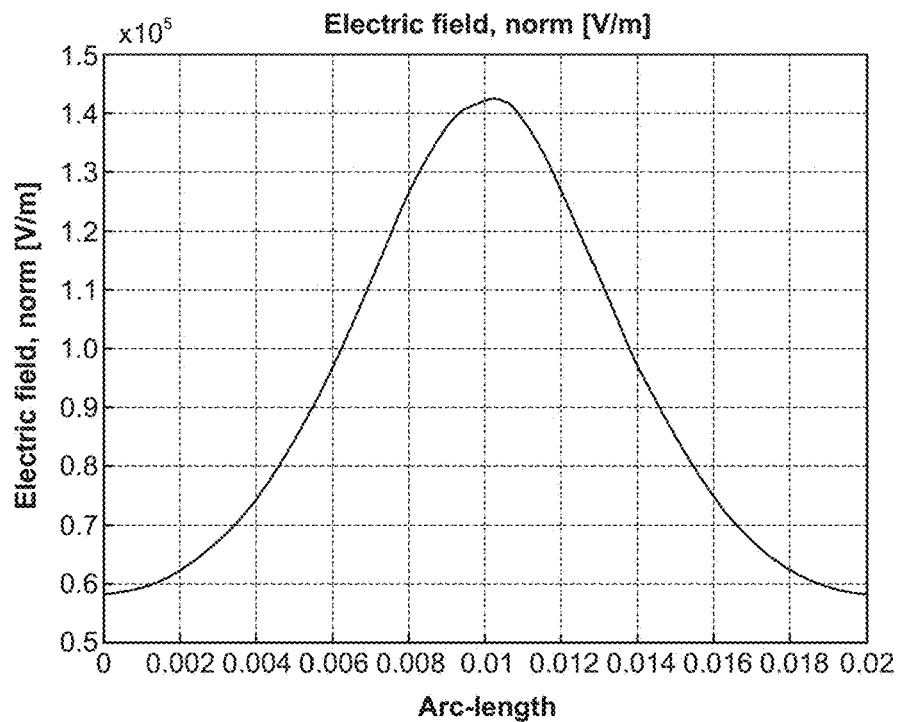
Figure 5D:
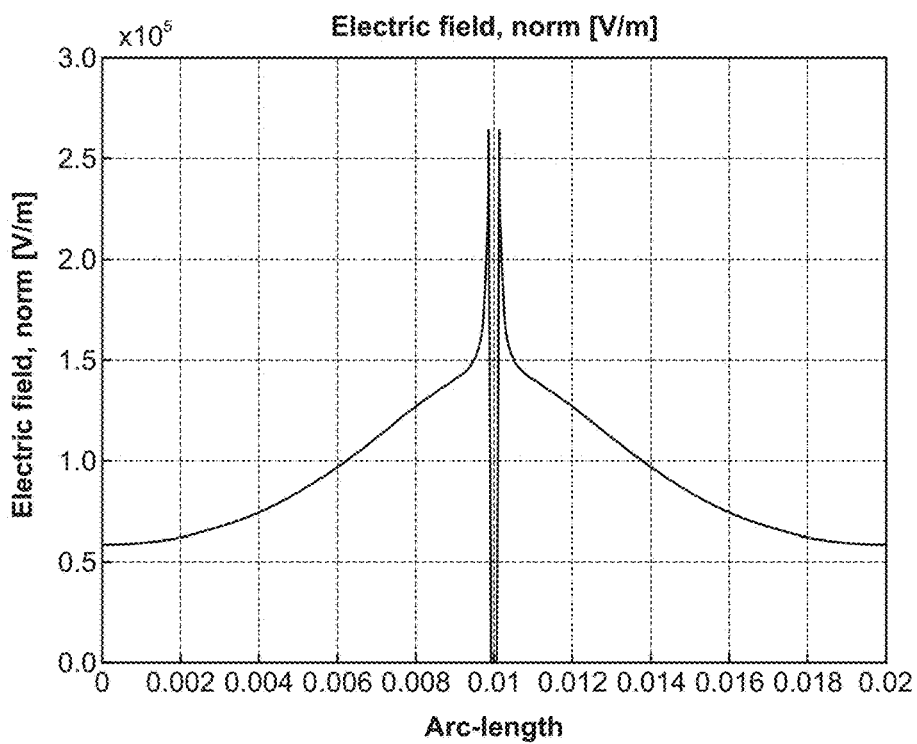
Figure 6A:
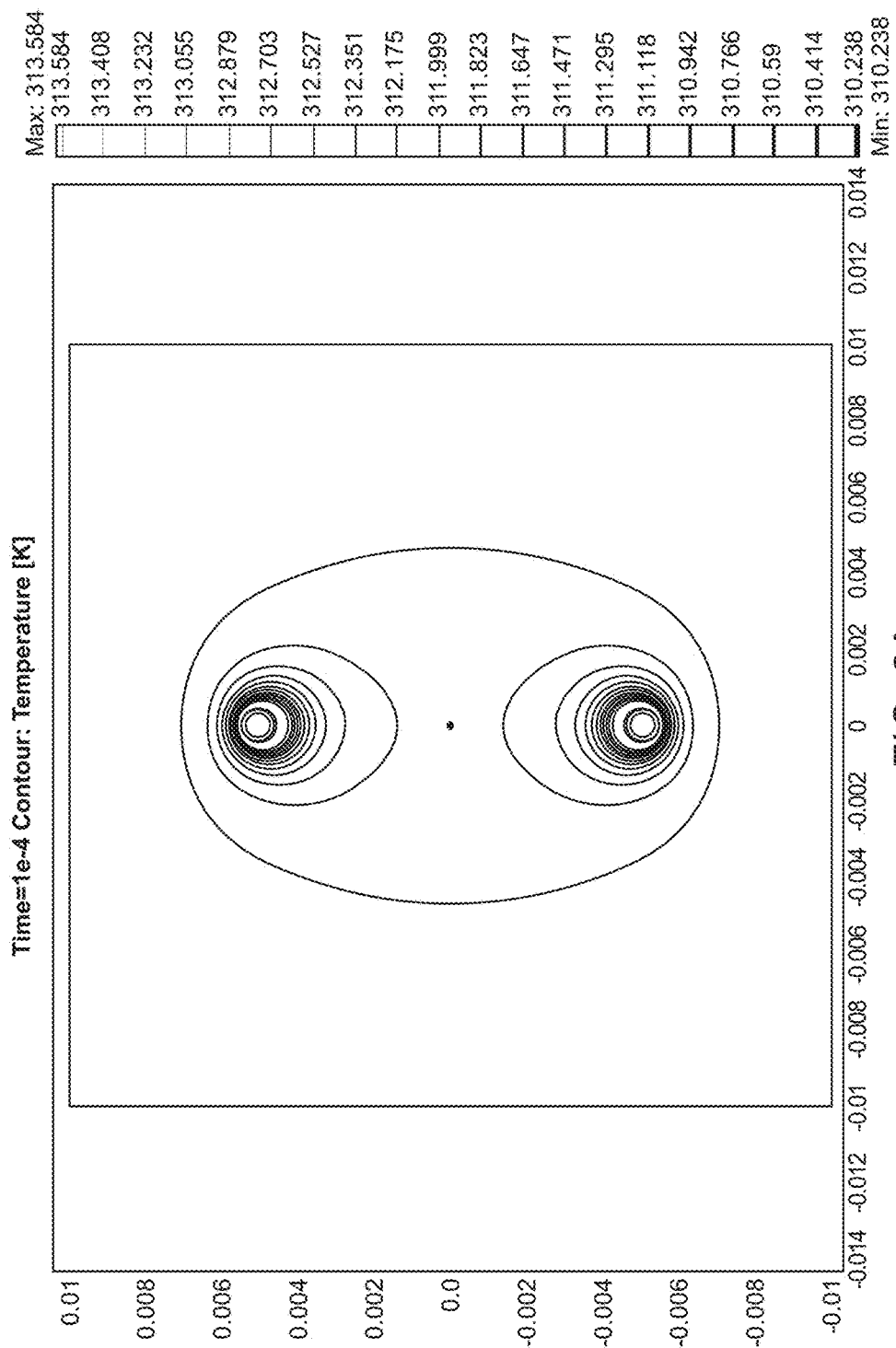
FIGS. 6A and 6B show the temperature distribution in the homogeneous (6A) and heterogenous (6B) models for prostate tissue with two electrodes.
Figure 6B:
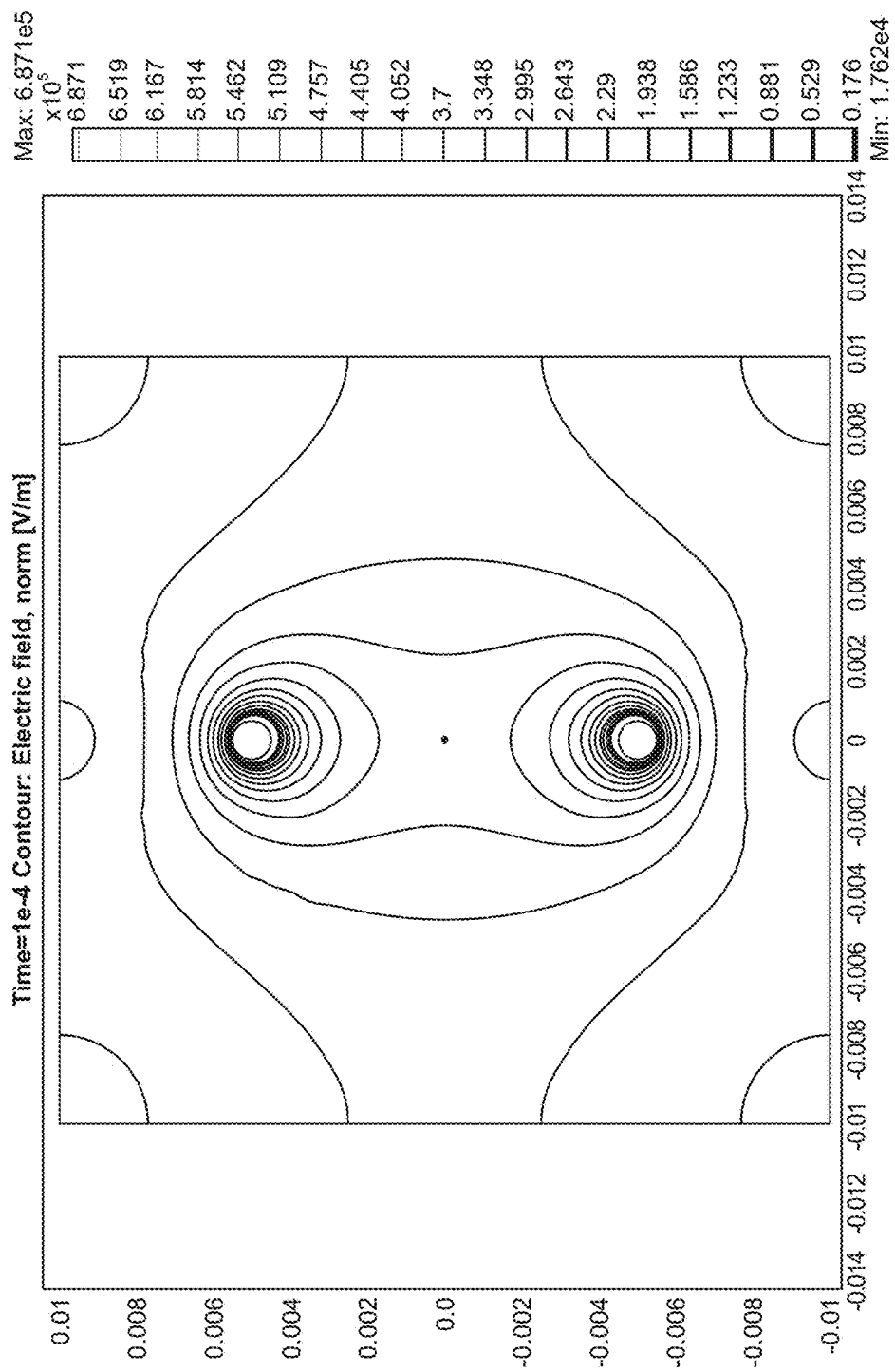

The remaining tissue in the rectangular sample above and below the electrodes receives a lessening effect, with the electric field forced to reach nearly $$0 \frac{V}{m}$$

at the edge of the tissue sample. However, it is important to note, in the location between the electrodes, where the nerve would be in the heterogeneous model, that the electric field does not quite reach zero, which is the desired effect. This can be seen in the plot of the electric field along a vertical cross section of the homogeneous model (FIG. 5A). It only reaches a minimum of $$1.45E5 \frac{V}{m}.$$

The electric field in the heterogeneous prostate (FIG. 4B) is exceptionally different than in the homogeneous prostate (FIG. 4A).

The maximum electric field is $$1.853E6 \frac{V}{m},$$

which is more than in the homogeneous model. In the heterogeneous model, the myelin receives the absolute highest levels of electric field in the entire sample. The electrodes themselves have substantially different readings. At $$1.7E6 \frac{V}{m},$$

the electric field in the myelin is almost a magnitude more than the maximum in the homogeneous model. The electric field elsewhere is low, beyond the immediate vicinity of the electrodes. The plots (FIGS. 5B and 5D) also show that the axon receives the lowest levels of electric field, reaching zero. This implies that the myelin insulates the axon from the effect of the electric field. Because axons are able to remyelinate themselves (W. F. Blakemore, "Remyelination by Schwann cells of axons demyelinated by intraspinal injection of 6-aminonicotinamide in the rat," *Journal of Neurocytology*, vol. 4, December 1975, pp. 745-757), these results suggest that the nerve structure should be able to fully recover even if the myelin is damaged. This plot demonstrates the importance of heterogeneous models to understand the effect of irreversible electroporation on the nervous system.

These results explain the outcome in the trials utilizing NTIRE to treat prostate cancer (G. Onik, P. Mikus, and B. Rubinsky, "Irreversible electroporation: implications for prostate ablation," *Technology in cancer research & treatment*, vol. 6, August 2007, pp. 295-300). Nerves surrounding the prostate remained unharmed by the effects of electroporation. It is now understood why the nerves near the prostate survived. The myelin insulates the axons from the electric field. Even if damaged, the axons remyelinate via Schwann cells and all neurological functionality is retained.

Example 2

Figure 7A:
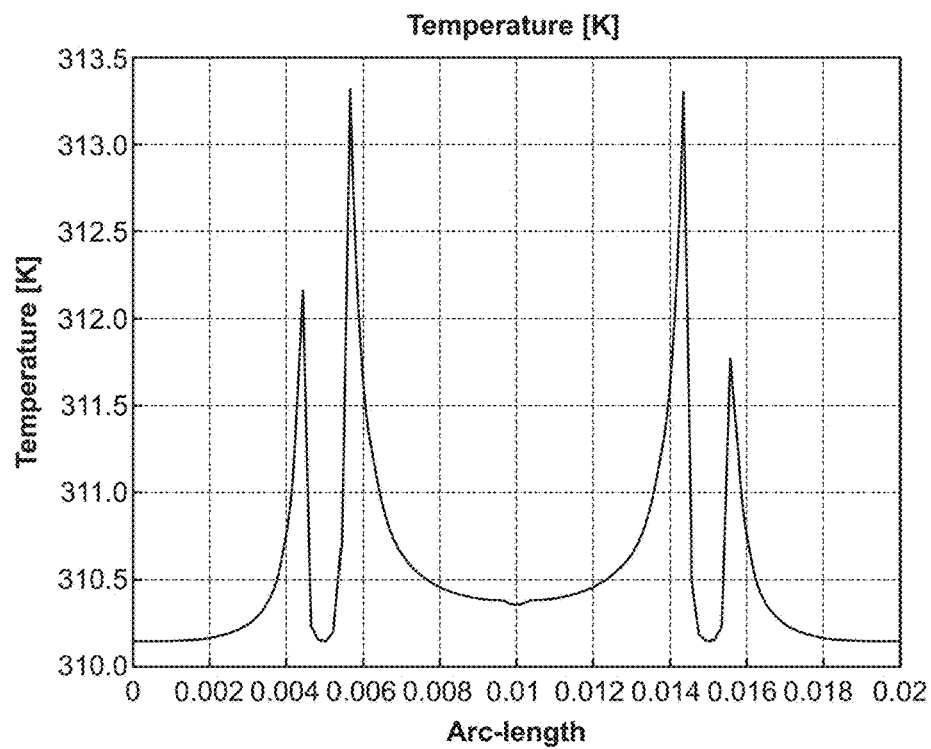
FIG. 7 includes four graphs which show temperature changes where graphs 7A and 7C show the changes with respect to homogeneous tissue and graphs 7B and 7D show temperature changes with heterogeneous tissue.
Figure 7B:
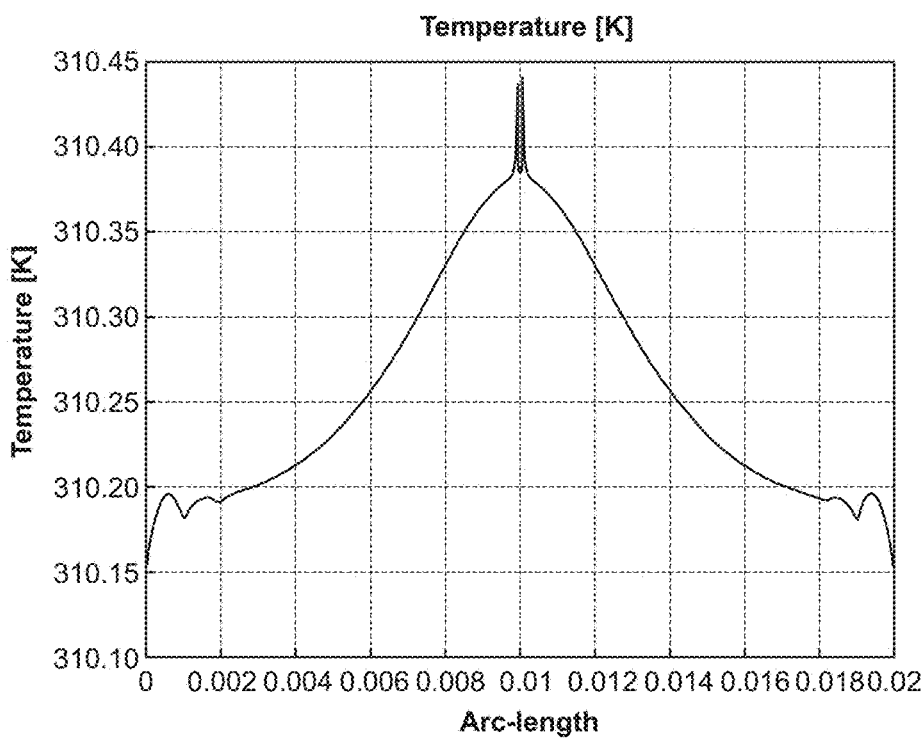
Figure 7C:
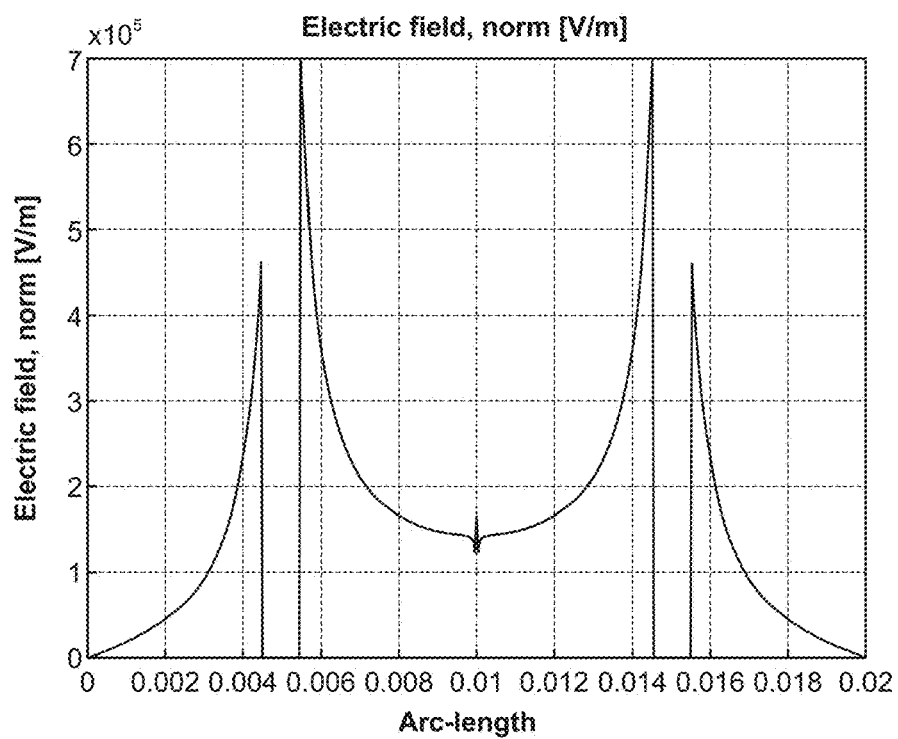
Figure 7D:
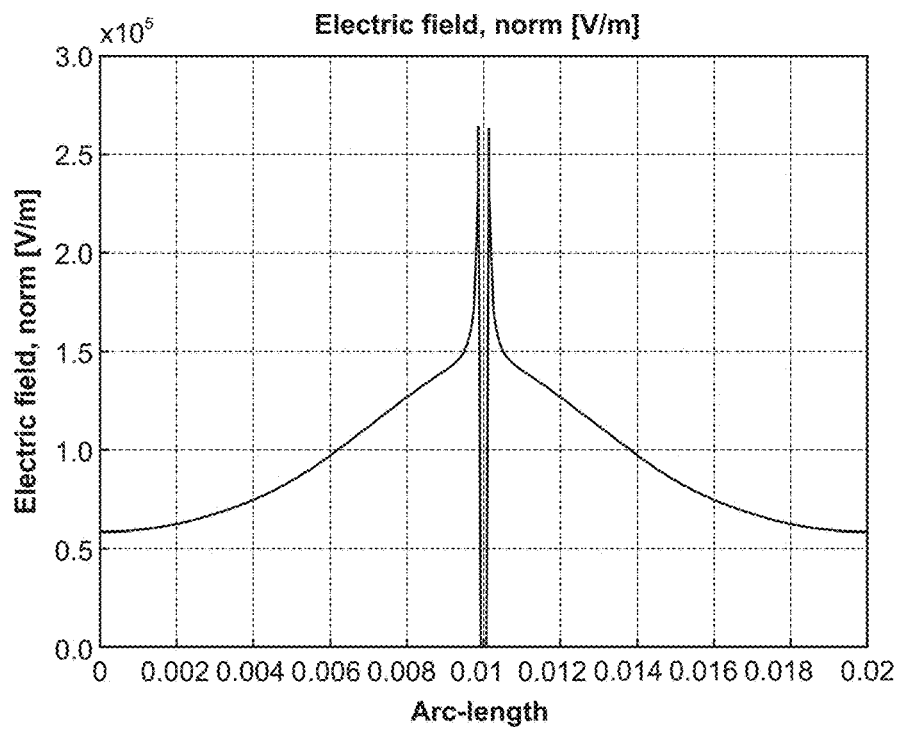

The methodology described above in Example 1 was used to analyze the prostate with a blood vessel which had a relatively small radius (e.g. less than 5 mm) which was placed in the center of a square section of prostate tissue. FIGS. 6A, 6B, 7A, 7B, 7C and 7D show the temperature distributions in the same manner as FIGS. 2A, 2B, 3A, 3B, 3C and 3D. The maximum temperature reached was 313.584K, while it was 313.431K for the homogeneous case. The blood vessel model has a temperature distribution between 310.238 and 313.584K. Because the maximum temperature reached is below 360.15K, the entire samples stays well below any temperature necessary for thermal damage. This means that absolutely none of the tissue receives any thermal damage. However, it is important to note that an elevated temperature does exist, but only in the immediate vicinity of the electrodes (FIG. 7A).

The electrical fields in this case are depicted in FIGS. 7 and 8 in the same manner as FIGS. 4 and 5.

The maximum electric field of the blood vessel in the prostate (FIG. 7) is lower than the homogeneous case. The homogeneous prostate reached $$6.964E5 \frac{V}{m},$$

while the prostate with a blood vessel reached $$6.87E5 \frac{V}{m}.$$

Additionally, there is a slight rise in the electric field in the vicinity of the blood vessel. This occurs because the electrical conductivity of the blood vessel is slightly lower than that of prostate tissue. Nevertheless it receives a low level of electric field, indicating that during clinical trials, blood vessels in the vicinity of a tumor would be unharmed by the effects of the electroporation.

Example 3

Figure 8B:
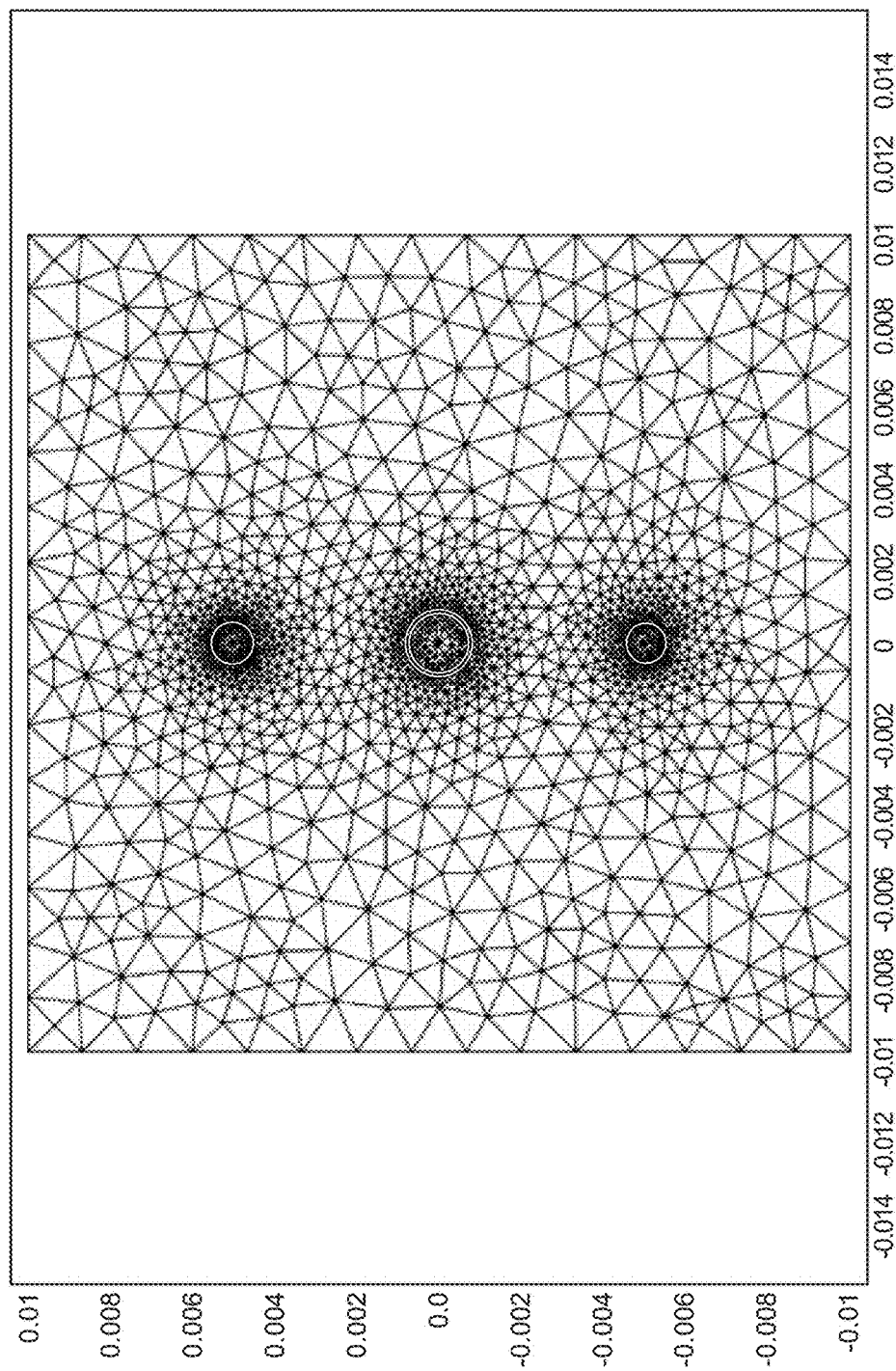

The methodology of Example 1 above was used to investigate the effects of electroporation on breast tissue. The model included a section of fatty breast tissue in the homogeneous model. In the heterogeneous model a gland surrounded by myoepithelial cells was included in the breast tissue (FIGS. 8A and 8B). The breast gland was 0.7 mm in radius (J. Rusby et al., "Breast duct anatomy in the human nipple: three-dimensional patterns and clinical implications," *Breast Cancer Research and Treatment*, vol. 106, January 2007, pp. 171-9.) and the surrounding layer of myoepithelial cells were 0.13 mm in thickness. The gland and myoepithelial cells were centered within a square section of breast tissue.

Figure 9A:
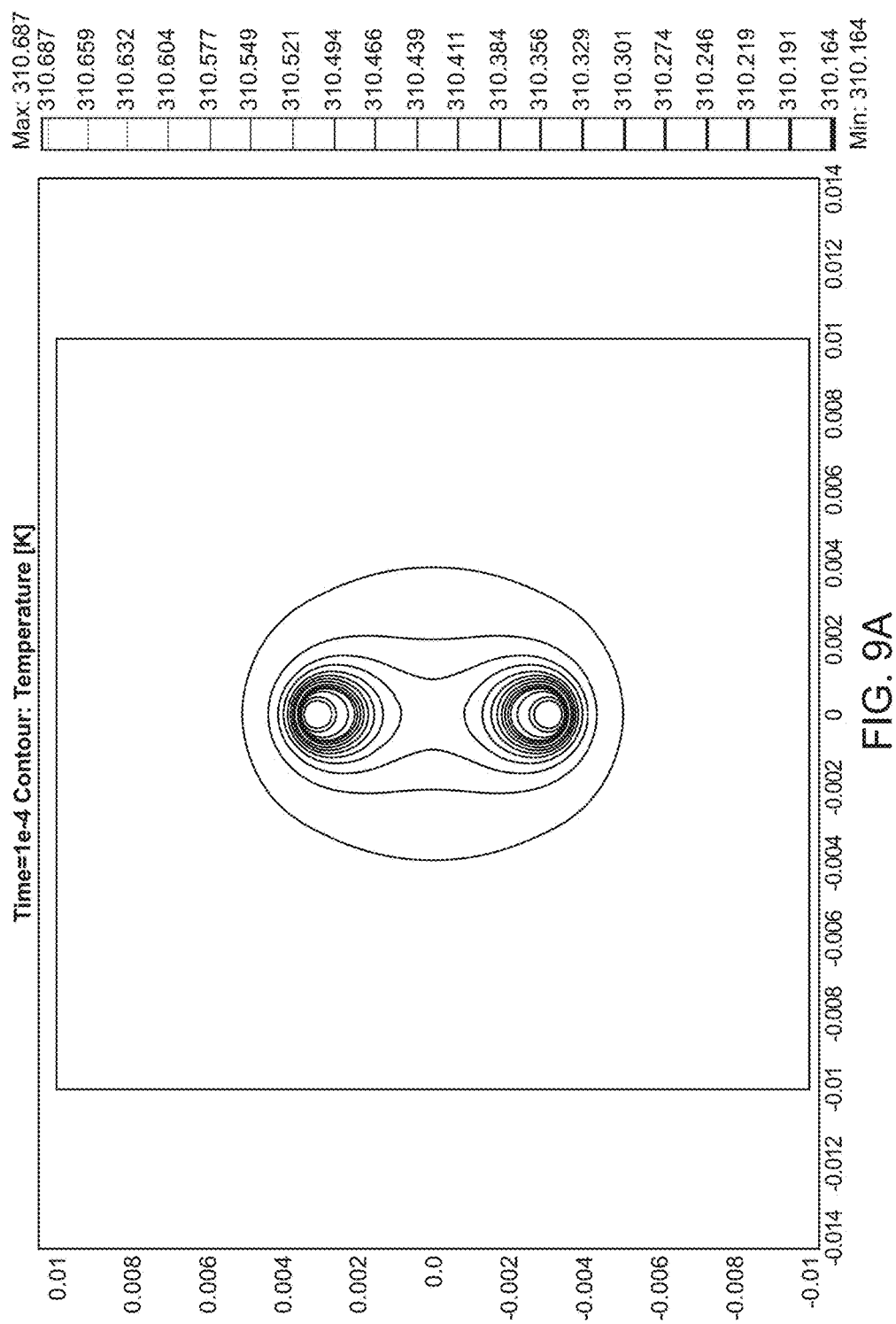
FIGS. 9A and 9B show the temperature distribution in the homogeneous (9A) and heterogenous (9B) models for prostate tissue with two electrodes.
Figure 9B:
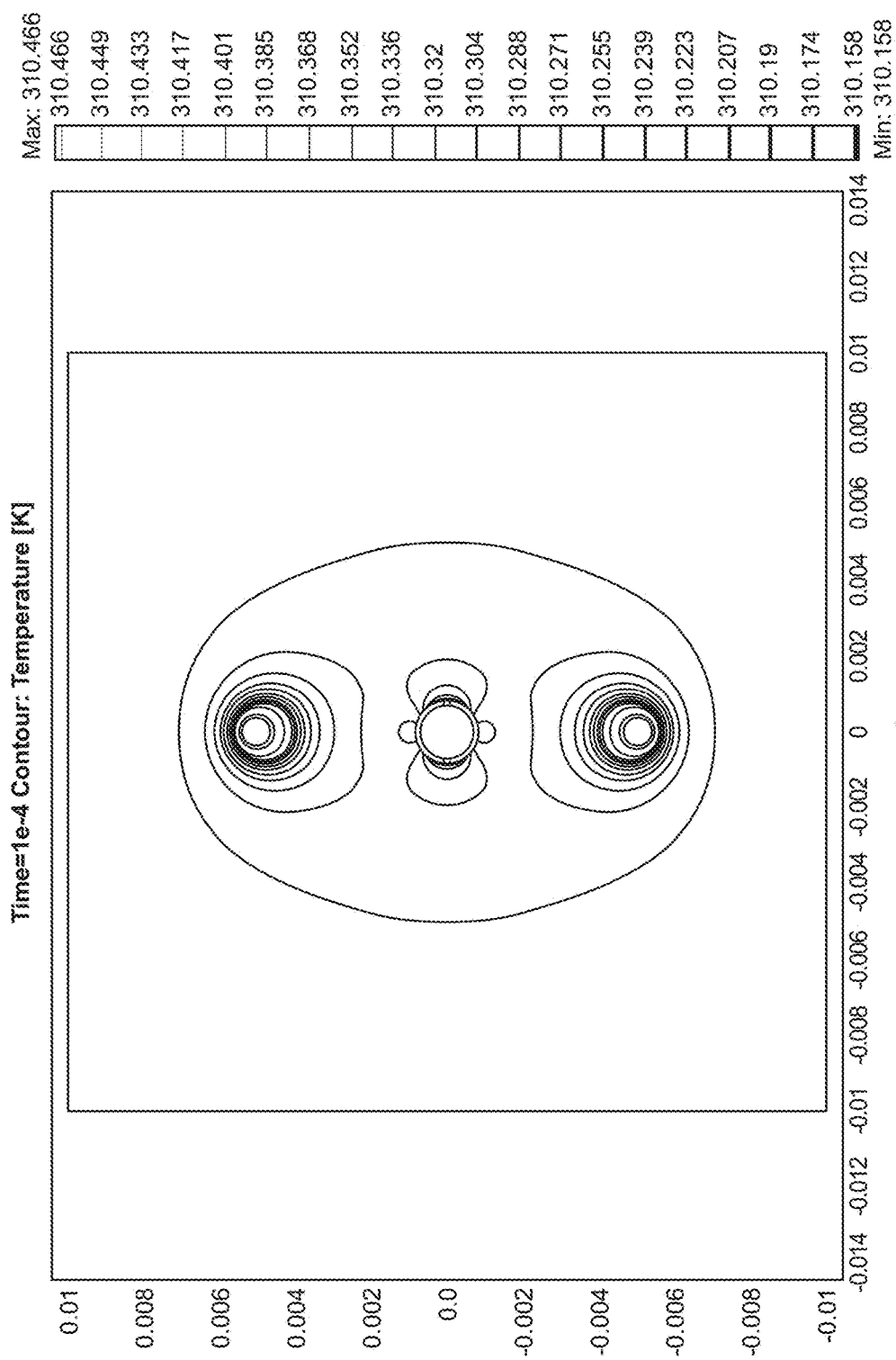
Figure 10A:
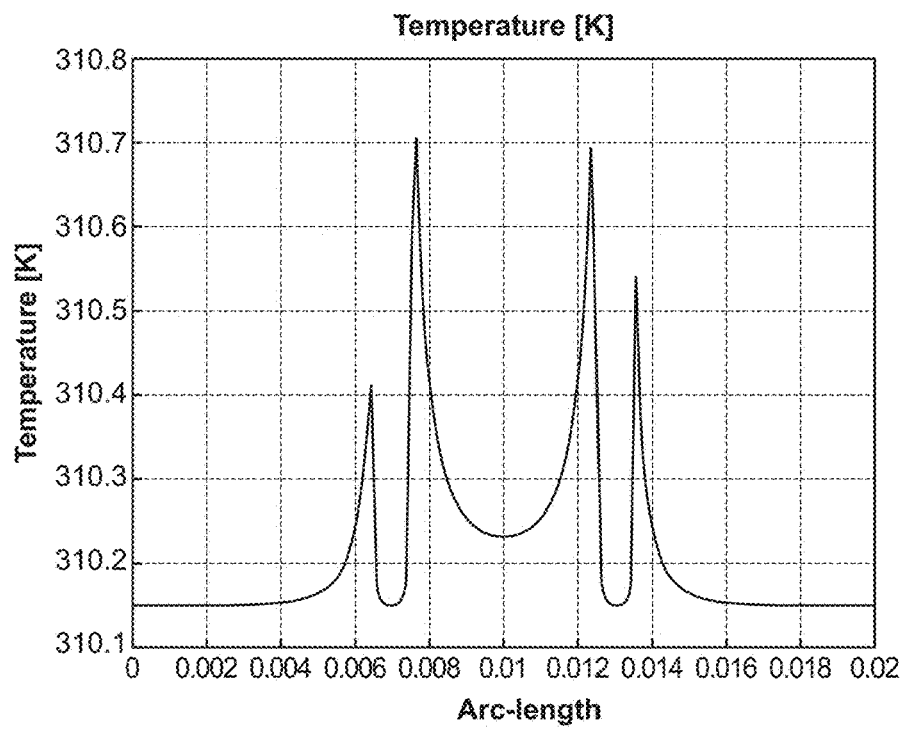
FIG. 10 includes four graphs which show temperature changes where graphs 10A and 10C show the changes with respect to homogeneous tissue and graphs 10B and 10D show temperature changes with heterogeneous tissue.
Figure 10B:
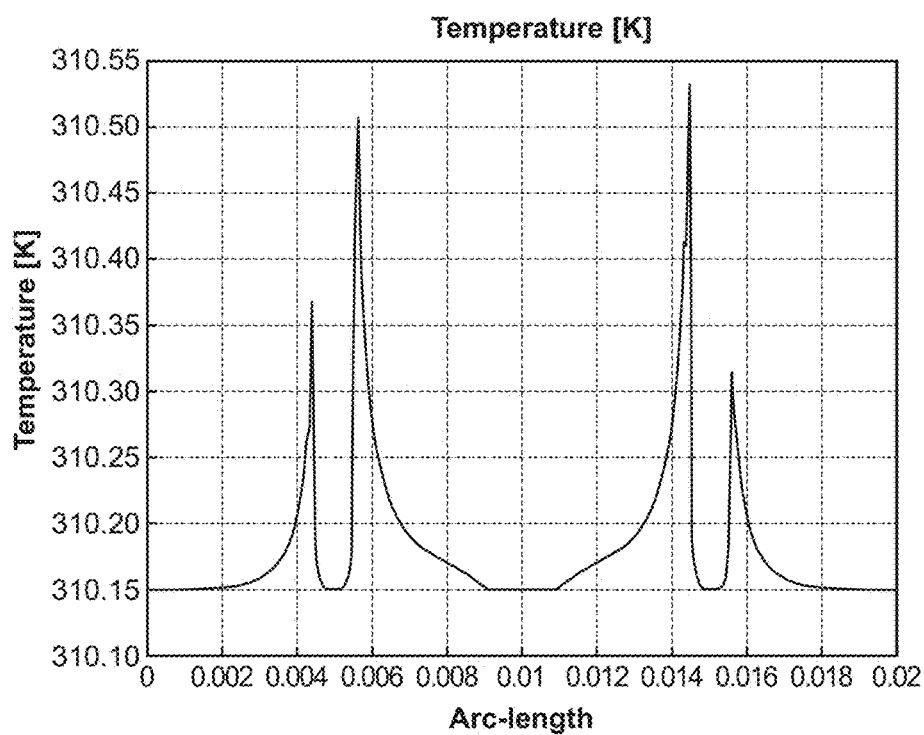
Figure 10C:
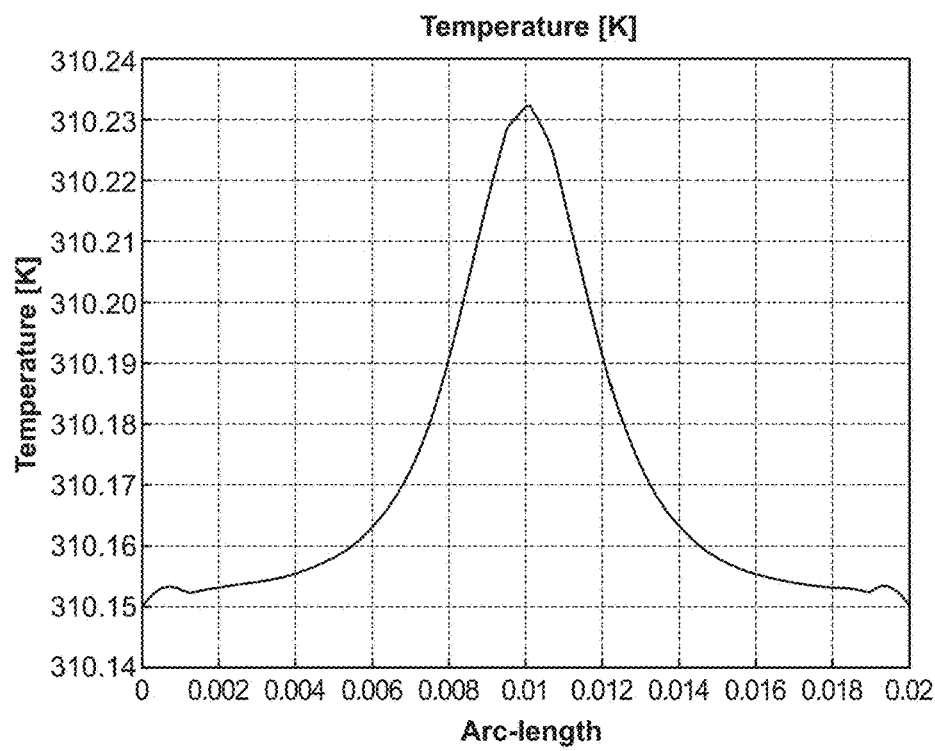
Figure 10D:
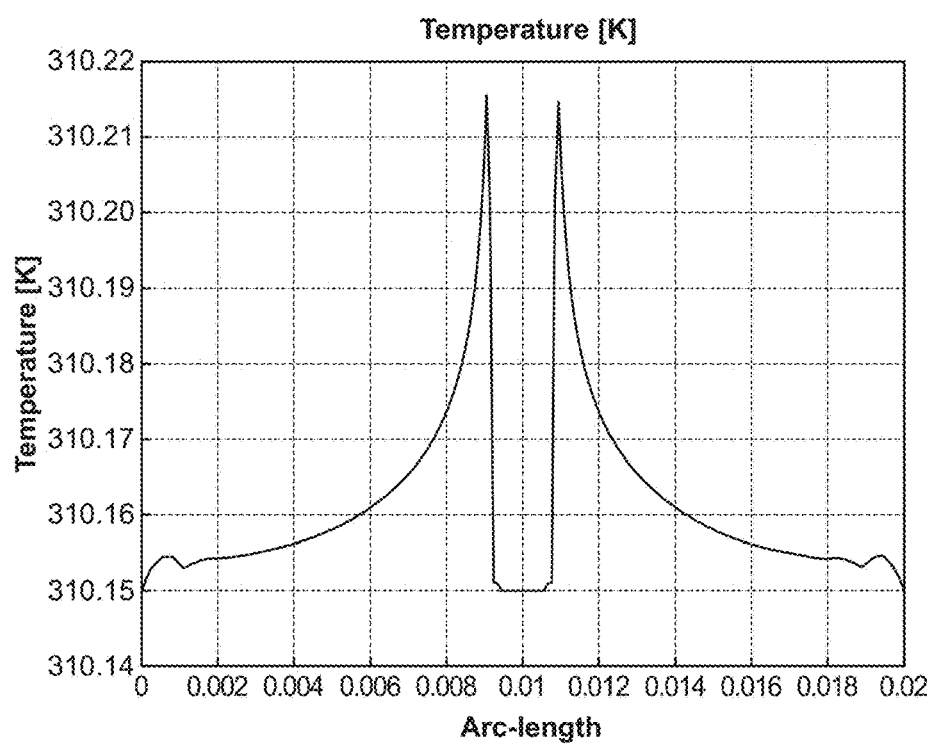
Figure 11A:
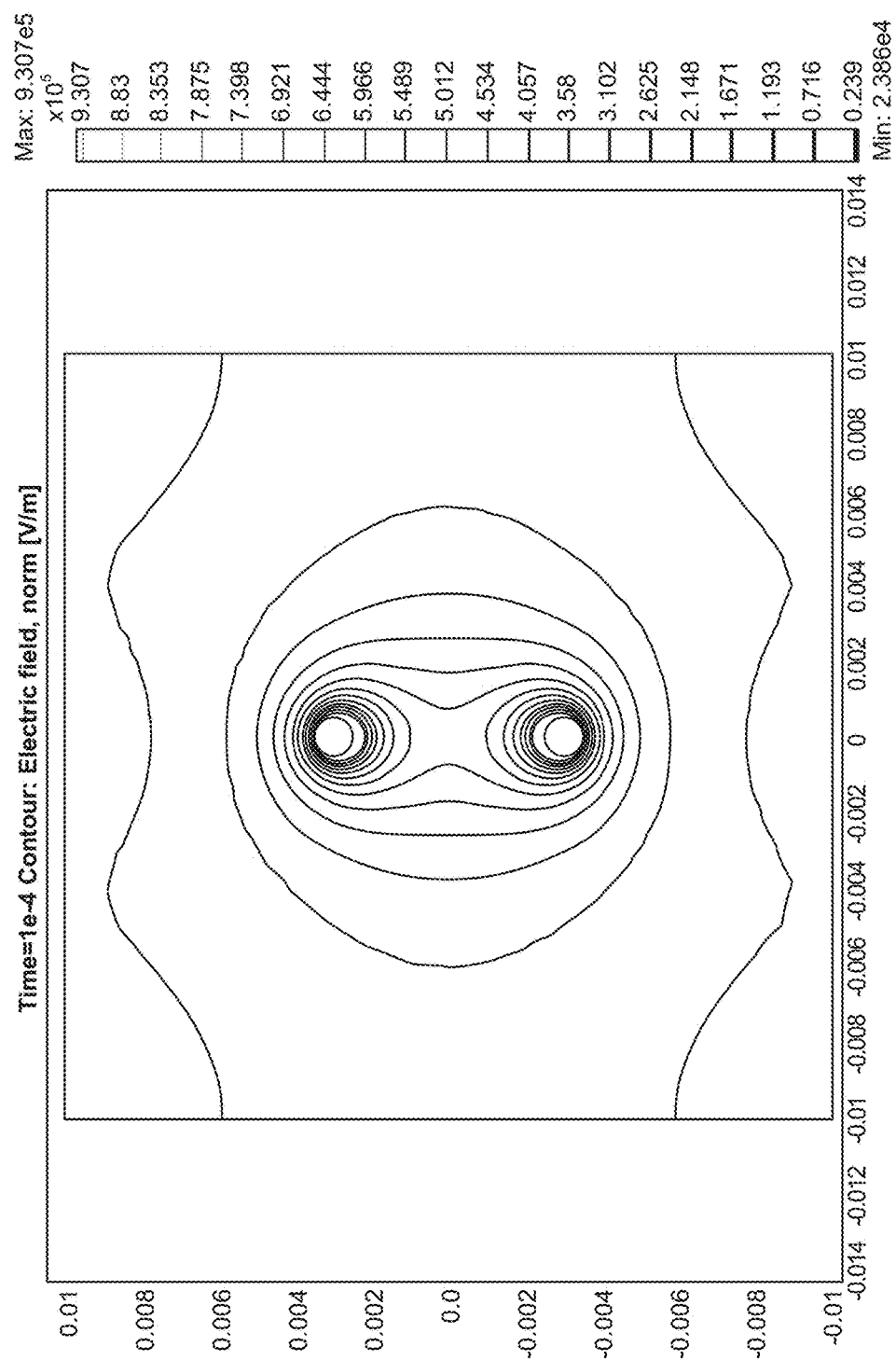
FIGS. 11A and 11B show the temperature distribution in the homogeneous (11A) and heterogenous (11B) models for prostate tissue with two electrodes.
Figure 11B:
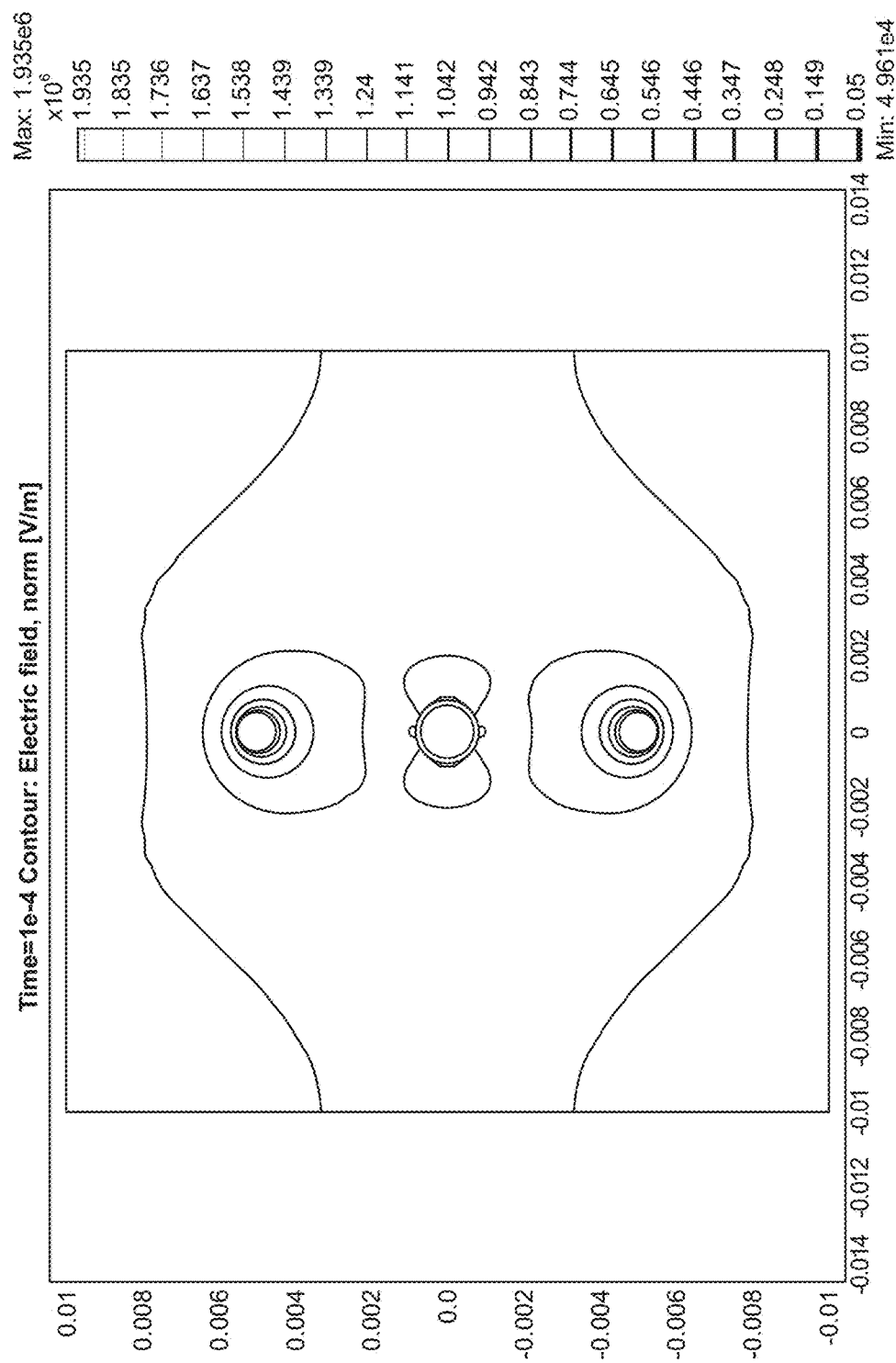
Figure 12A:
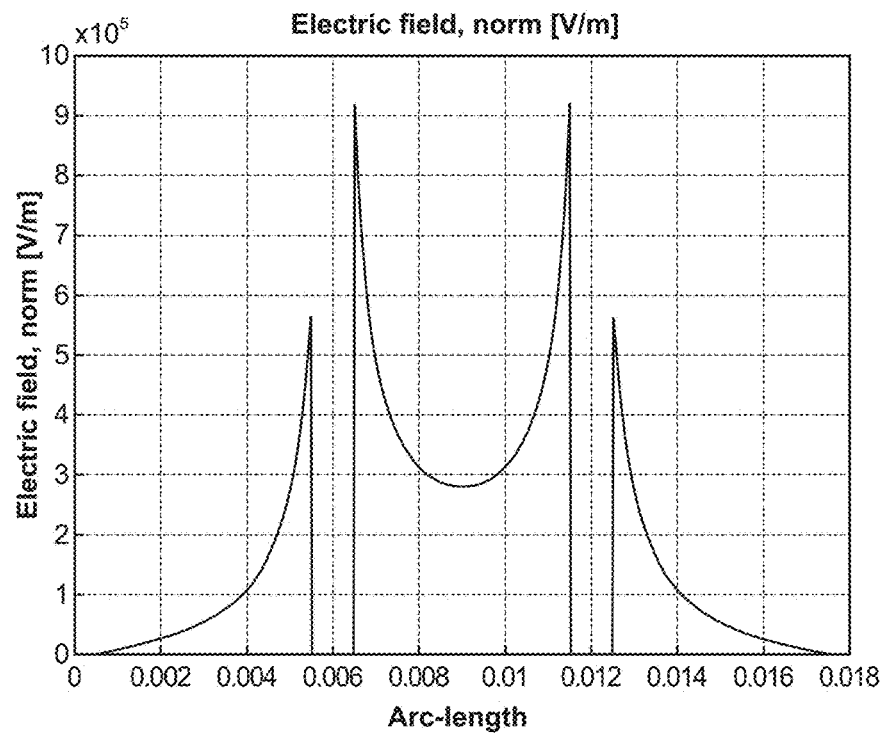
FIG. 12 includes four graphs which show temperature changes where graphs 12A and 12C show the changes with respect to homogeneous tissue and graphs 12B and 12D show temperature changes with heterogeneous tissue.
Figure 12B:
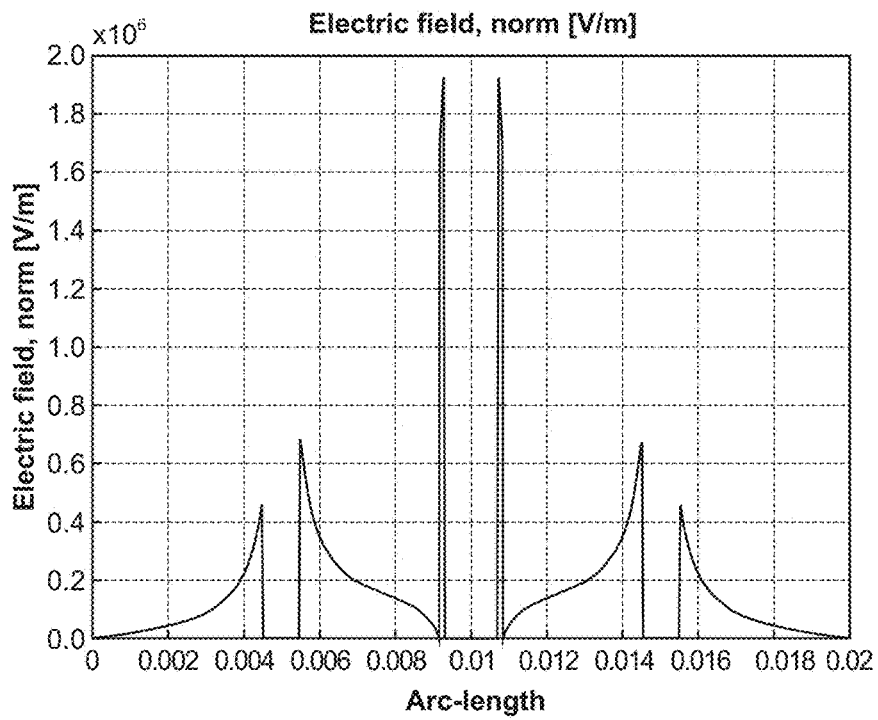
Figure 12C:
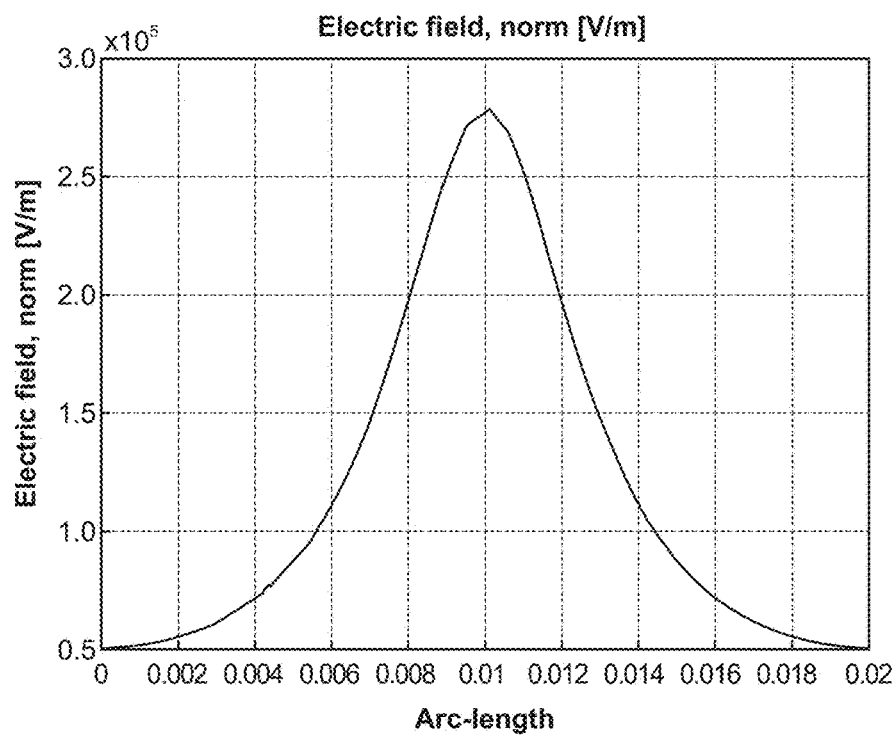
Figure 12D:
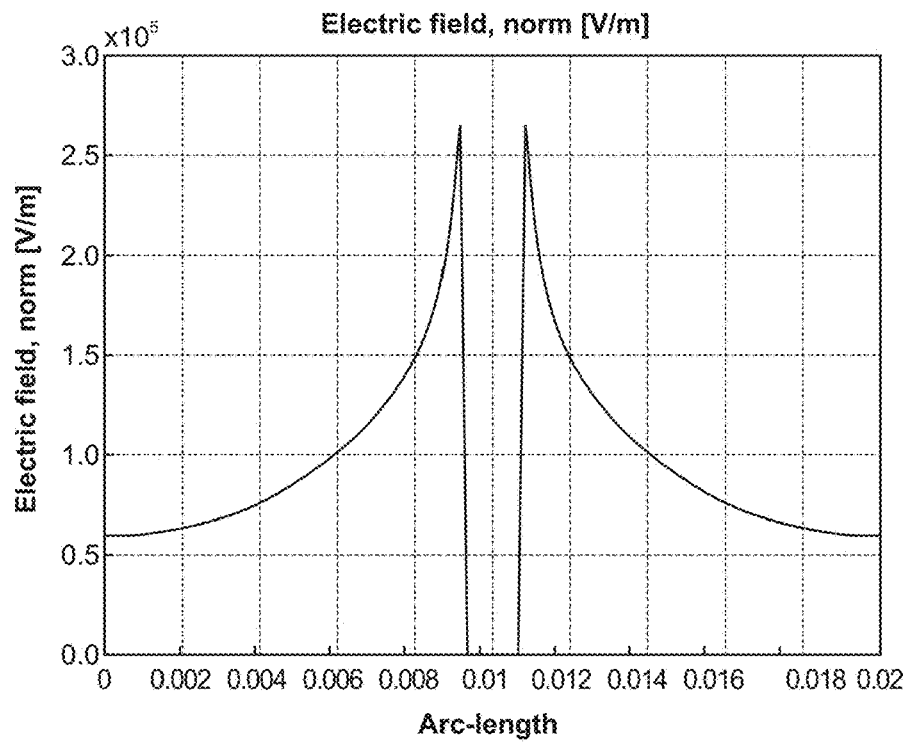

FIGS. 9 and 10 are presented in the same manner as FIGS. 2 and 3 and FIGS. 11 and 12 in the same manner as FIGS. 4 and 5. FIG. 10 shows that in the vertical plane the highest temperature reached in the homogeneous model is 310.687K, only 0.537 degrees higher than body temperature. In the heterogeneous case, however, the maximum temperature, 310.466K, is even lower. There is no portion of tissue in the entire sample that reaches temperature levels required for thermal damage. The horizontal cross section yields a vast difference between the temperature distribution in the homogeneous and heterogeneous cases (FIG. 10). The homogeneous model reaches a maximum at the location between the electrodes, but the heterogeneous model dips to a minimum.

In the homogeneous model the maximum electric field reaches $$9.307E5 \frac{V}{m}.$$

The maximum electric field in the heterogeneous model, $$1.935E6 \frac{V}{m},$$

is slightly higher. However, the electric field between the electrodes is very different.

In the heterogeneous model the electric field reaches zero at the center of the gland (FIG. 12). However, in the homogeneous model, the electric field only goes as low as $$2.9E5 \frac{V}{m}.$$

Additionally, in the homogeneous model, the highest electric field occurs at the electrodes. But in the heterogeneous model, the highest electric field is within the myoepithelial cells and is followed distantly by the electric field near the electrodes. This, however, does not pose a threat to the physiological function of the ducts because myoepithelial cells are known to regenerate (S. TAKAHASHI et al., "Regeneration of myoepithelial cells in rat submandibular glands after yttrium aluminium garnett laser irradiation," *International Journal of Experimental Pathology*, vol. 78, 1997, pp. 91-99).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

REFERENCES

[1] J. Edd et al., "In vivo results of a new focal tissue ablation technique: irreversible electroporation," *Biomedical Engineering, IEEE Transactions on*, vol. 53, 2006, pp. 1409-1415.
[2] S. Belov, "Effects of high-frequency current parameters on tissue coagulation," *Biomedical Engineering*, vol. 12, July 1978, pp. 209-211.
[3] R. C. Lee, "Cell injury by electric forces," *Annals of the New York Academy of Sciences*, vol. 1066, December 2005, pp. 85-91.
[4] R. Fpster, R. Bihrle, and N. Sanghvi, "High-intensity focused ultrasound in the treatment of prostatic disease," *Eur. Urol.*, vol. 23, 1993, pp. 44-47.
[5] L. W. Organ, "Electrophysiologic principles of radiofrequency lesion making," Applied *Neurophysiology*, vol. 39, pp. 69-76.
[6] S. G. Bown, "Phototherapy in tumors," *World Journal of Surgery*, vol. 7, November 1983, pp. 700-9.
[7] B. Rubinsky, G. Onik, and P. Mikus, "Irreversible electroporation: a new ablation modality—clinical implications," *Technology in cancer research & treatment*, vol. 6, Feb. 2007, pp. 37-48.
[8] B. Al-Sakere et al., "Tumor Ablation with Irreversible Electroporation," *PLoS ONE*, vol. 2, 2007, p. e1135.
[9] G. Onik, P. Mikus, and B. Rubinsky, "Irreversible electroporation: implications for prostate ablation," *Technology in cancer research & treatment*, vol. 6, August 2007, pp. 295-300.
[10] R. V. Davalos, B. Rubinsky, and L. M. Mir, "Theoretical analysis of the thermal effects during in vivo tissue electroporation," *Bioelectrochemistry*, vol. 61, October 2003, pp. 99-107.
[11] R. Davalos, B. Rubinsky, and D. Otten, "A feasibility study for electrical impedance tomography as a means to monitor tissue electroporation for molecular medicine," Biomedical Engineering, *IEEE Transactions on*, vol. 49, 2002, pp. 400-403.
[12] Rafael Davalos and Boris Rubinsky, "Temperature considerations during irreversible electroporation," *International Journal of Heat and Mass Transfer*, May. 2008.
[13] F. Montorsi et al., "Recovery of spontaneous erectile function after nerver-sparing radical retropubic prostatectomy with and without early intracavernous injections of alprostadil: results of a prospective, randomized trial," *The Journal of Urology*, vol. 158, October 1997, pp. 1408-1410.
[14] S. Higgins and B. G. Haffty, "Pregnancy and lactation after breast-conserving therapy for early stage breast cancer," *Cancer*, vol. 73, April 1994, pp. 2175-80.
[15] J. C. Lasry et al., "Depression and body image following mastectomy and lumpectomy," *Journal of Chronic Diseases*, vol. 40, 1987, pp. 529-34.
[16] D. Andreuccetii, R. Fossi, and C. Petrucci, "Dielectric Properties of Body Tissues: Output data," *Italian National Research Council Institute for Applied Physics IFAC*; http://niremf.ifac.cnr.it/tissprop/htmlclie/htmlclie.htm#atsftag.
[17] M. Villapecellin-Cid, L. Rao, and J. Reina-Tosina, "Ranvier nodes impedance match with internodal transmission lines of myelinated axons," *Engineering in Medicine and Biology Society, 2003. Proceedings of the 25th Annual International Conference of the IEEE*, 2003, pp. 1905-1908 Vol. 2.
[18] B. J. Roth and J. P. Wikswo, "The magnetic field of a single axon. A comparison of theory and experiment.," *Biophys. J.*, vol. 48, July 1985, pp. 93-109.
[19] Hassan N et al., "Numerical study of induced current perturbations in the vicinity of excitable cells exposed to extremely low frequency magnetic fields,"*Physics in Medicine and Biology*, vol. 48, 2003, pp. 3277-3293.
[20] A. M. Campbell and D. V. Land, "Dielectric properties of female human breast tissue measured in vitro at 3.2 GHz," *Physics in Medicine and Biology*, vol. 37, 1992, pp. 193-210.
[21] Yusheng Feng et al., "Nanoshell-Mediated Laser Surgery Simulation for Prostate Cancer Treatment," *Engineering with Computers*.
[22] S. DeMarco et al., "Computed SAR and thermal elevation in a 0.25-mm 2-D model of the human eye and head in response to an implanted retinal stimulator—part I: models and methods," *Antennas and Propagation, IEEE Transactions on*, vol. 51, 2003, pp. 2274-2285.

[23] Howorka K. et al., "Thermal conductivity of minke whale blubber," *Journal of Thermal Biology*, vol. 21, April 1996, pp. 123-128.

[24] M. P. Robinson et al., "New materials for dielectric simulation of tissues," *Physics in Medicine and Biology*, vol. 36, 1991, pp. 1565-1571.

[25] F. Fidanza, "Body fat in adult man: semicentenary of fat density and skinfolds," *Acta Diabetologica*, vol. 40, October 2003, pp. s242-s245.

[26] F. O. Dosekun, "The measurement of metabolic and vascular responses in the thyroid gland with observations on its responses to insulin, glucose and adrenaline," *The Journal of Physiology*, vol. 157, August 1961, pp. 504-512.

[27] M. A. Kolka, W. L. Holden, and R. R. Gonzalez, "Heat exchange following atropine injection before and after heat acclimation," *J Appl Physiol*, vol. 56, April 1984, pp. 896-899.

[28] C. R. Moreira et al., "Quantitative age-related differences in human sublingual gland," *Archives of Oral Biology*, vol. 51, November 2006, pp. 960-966.

[29] Kwok, Jeni and Krzyspiak, Joanna, "Thermal Imaging and Analysis for Breast Tumor Detection," *Computer-Aided Engineering: Applications to Biomedical Processes*, July 2007.

[30] P. Prakash et al., "Measurement of the specific heat capacity of liver phantom," *Physiological Measurement*, vol. 27, October 2006, pp. N41-N46.

[31] L. Sun, J. Schiano, and N. Smith, "Novel adaptive control system for ultrasound hyperthermia treatment of prostate disease," *Ultrasonics, 2003 IEEE Symposium on,* 2003, pp. 1274-1277 Vol. 2.

[32] J. Valvano and B. Chitsabesan, "Thermal conductivity and diffusivity of arterial wall and atherosclerotic plaque," *Lasers in the Life Sciences*, vol. 1, 1987, pp. 219-229.

[33] Elad Maor, Antoni Ivorra, and Boris Rubinsky, "Intravascular Irreversible Electroporation: Theoretical and Experimental Feasibility Study," *proceedings of the IEEE EMBC 2008 Conference,* 2008.

[34] A. Takenaka et al., "Variation in course of cavernous nerve with special reference to details of topographic relationships near prostatic apex: Histologic study using male cadavers," *Urology*, vol. 65, January 2005, pp. 136-142.

[35] J. Schroder, "Altered ratio between axon diameter and myelin sheath thickness in regenerated nerve fibers," *Brain Research*, vol. 45, October 1972, pp. 49-65.

[36] W. F. Blakemore, "Remyelination by Schwann cells of axons demyelinated by intraspinal injection of 6-aminonicotinamide in the rat," *Journal of Neurocytology*, vol. 4, December 1975, pp. 745-757.

[37] J. Rusby et al., "Breast duct anatomy in the human nipple: three-dimensional patterns and clinical implications," *Breast Cancer Research and Treatment*, vol. 106, January 2007, pp. 171-9.

[38] S. TAKAHASHI et al., "Regeneration of myoepithelial cells in rat submandibular glands after yttrium aluminium garnett laser irradiation," *International Journal of Experimental Pathology*, vol. 78, 1997, pp. 91-99.

That which is claimed is:

1. A method of targeting cancer cells, comprising the steps of:
   (a) identifying cancer cells to be ablated in a target area, wherein the target area comprises heterogenous tissue comprising nerve tissue surrounded by myelin layers;
   (b) placing a first electrode and a second electrode such that the target area is positioned between the first and second electrodes;
   (c) applying electrical pulses between the first and second electrodes in an amount which compensates for tissue heterogeneity, and is sufficient to irreversibly electroporate the cancer cells in the target area; wherein voltage, wattage and duration of the electrical pulses are maintained within ranges which avoid damage to the nerve tissue in the target area; and
   (d) monitoring temperature of the heterogeneous tissue and adjusting the electrical pulses to maintain the temperature at 50° C. or less for a period of time that avoids thermal damage to cells of the heterogeneous tissue.

2. The method of claim 1, wherein:
   a size, shape, and relative position of the first electrode and the second electrode are determined prior to placing step (b) so as to avoid damage to the nerve tissue in the target area and avoid thermal damage to cells in the target area.

3. The method of claim 1, further comprising:
   infusing a material into the heterogenous tissue prior to applying the electrical pulses.

4. The method of claim 3, wherein the material is a chemotherapeutic agent.

5. The method of claim 3, wherein the material is an imaging agent.

6. The method of claim 1, wherein the first electrode and second electrode are circular in shape; and
   wherein the first and second electrodes are positioned within less than 2 cm of each other.

7. A method of targeting cancer cells, comprising the steps of:
   (a) identifying cancer cells to be ablated in a target area, wherein the target area comprises heterogeneous tissue comprising nerve tissue surrounded by myelin layers;
   (b) placing a first electrode and a second electrode such that the target area is positioned between the first and second electrodes; and
   (c) monitoring temperature of the heterogeneous tissue and adjusting electrical pulses from the first and second electrodes to ablate the cancer cells without damaging the nerve tissue, and maintain temperature at 50° C. or less for a period of time thereby avoiding thermal damage to cells of the heterogeneous tissue.

8. The method of claim 7, further comprising:
   infusing a material into the target area prior to applying the electrical pulses.

9. The method of claim 8, wherein the material is a chemotherapeutic agent.

10. The method of claim 8, wherein the material is an imaging agent.

11. A method of ablating cancer cells, comprising the steps of:
    (a) identifying cancer cells to be ablated in a target area, wherein the target area comprises heterogeneous tissue comprising nerve tissue surrounded by myelin layers;
    (b) placing a first electrode and a second electrode such that the target area is positioned between the first and second electrodes; and
    (c) monitoring temperature of the heterogeneous tissue and adjusting electrical pulses from the first and second electrodes to ablate the cancer cells without damaging the nerve tissue, and maintain temperature at 50° C. or less for a period of time that avoids thermal damage to cells of the heterogeneous tissue, wherein the first electrode and second electrode are circular in shape; and wherein the first and second electrodes are positioned within less than 2 cm of each other.

12. The method of claim 11, further comprising:
infusing a material into the targeted area prior to applying the electrical pulses.

13. The method of claim 12, wherein the material is a chemotherapeutic agent.

14. The method of claim 12, wherein the material is an imaging agent.

* * * * *